United States Patent
Lee et al.

(10) Patent No.: US 9,073,956 B1
(45) Date of Patent: Jul. 7, 2015

(54) DIHYDRO-1H-PHOSPHOLE 1-OXIDE DERIVATIVES AND PREPARATION METHOD THEREOF

(71) Applicant: KNU-INDUSTRY COOPERATION FOUNDATION, Chuncheon-si (KR)

(72) Inventors: Phil Ho Lee, Chuncheon-si (KR); Tae Kyu Ryu, Chuncheon-si (KR); Sang June Park, Chuncheon-si (KR)

(73) Assignee: KNU-INDUSTRY COOPERATION FOUNDATION (KR)

( * ) Notice: Subject to any disclaimer, the term of this patent is extended or adjusted under 35 U.S.C. 154(b) by 0 days.

(21) Appl. No.: 14/595,448

(22) Filed: Jan. 13, 2015

(30) Foreign Application Priority Data

May 2, 2014 (KR) .......................... 10-2014-0053272

(51) Int. Cl.
*C07F 9/6571* (2006.01)
*C07F 9/6584* (2006.01)

(52) U.S. Cl.
CPC ....... *C07F 9/657181* (2013.01); *C07F 9/65844* (2013.01)

(58) Field of Classification Search
USPC .................................................... 558/80, 82
See application file for complete search history.

(56) References Cited

U.S. PATENT DOCUMENTS 4,272,278 A 6/1981 Beeny et al.

OTHER PUBLICATIONS

J. A. Miles, et al., Synthesis of Novel Phosphorus Heterocycles:1,3-Dihydro-2,1-Benzoxaphosphole 1-Oxides1,2, J. Org. Chem., 1982, pp. 1677-1682.
J. A. Miles, et al., Synthesis of Novel Phosphorus Heterocycles:2-Aryl-1-methyl-2,3-dihydro-1 H-2,1-benzazaphosphole 1-Oxides, J. Org. Chem., 1981, pp. 3486-3492.
Martin J. P. Harger, et al., Photolysis of Phenylphosphinic Azides having ortho Alkyl Substituents:Intramolecular Nitrene Insertion into C—H Bonds, J. Chem. Soc., 1991, pp. 1187-1188.
Sangjune Park, et al., Rhodium(III)-Catalyzed Oxidative Coupling through C—H Activation and Annulation Directed by Phosphonamide and Phosphinamide Group, The Royal Society of Chemistry, 2013, pp. 1-127.
Sangjune Park, et al., Rhodium-catalyzed oxidative coupling through C—H activation and annulation directed by phosphonamide and phosphinamide groups, Chem. Commun., 2013, pp. 8671-8673.

*Primary Examiner* — Kristin Vajda
(74) *Attorney, Agent, or Firm* — Cantor Colburn LLP

(57) ABSTRACT

Provided are novel dihydro-1H-phosphole 1-oxide derivatives and a preparation method thereof. More particularly, the dihydro-1H-phosphole 1-oxide derivatives include 1,3-dihydro-1H-2,1-oxaphosphole 1-oxide derivatives and 2,3-dihydro-1H-2,1-azaphosphole 1-oxide derivatives. Further, in the preparation method of a dihydro-1H-phosphole 1-oxide derivative according to the present invention, various phosphinine oxide derivatives may be prepared with high yield by a simple synthesis process by reacting a phosphinic derivative and a vinyl derivative with each other in the presence of a rhodium (Rh) catalyst, an oxidant, and a base.

12 Claims, No Drawings

DIHYDRO-1H-PHOSPHOLE 1-OXIDE DERIVATIVES AND PREPARATION METHOD THEREOF

CROSS-REFERENCE TO RELATED APPLICATIONS

This application claims priority under 35 U.S.C. §119 to Korean Patent Application No. 10-2014-0053272, filed on May 2, 2014, in the Korean Intellectual Property Office, the disclosure of which is incorporated herein by reference in its entirety.

TECHNICAL FIELD

The following disclosure relates to novel dihydro-1H-phosphole 1-oxide derivatives and a preparation method thereof, and more particularly, to dihydro-1H-phosphole 1-oxide derivatives including 1,3-dihydro-1H-2,1-oxaphosphole 1-oxide derivatives and 2,3-dihydro-1H-2,1-azaphosphole 1-oxide derivatives, and a preparation method thereof.

BACKGROUND

A heterocyclic compound configures a basic skeleton of a natural material, and an organic phosphorus compound has pharmacological and physiological activities. The organic phosphorus compound is significantly associated with biological phenomena, such that developments of and researches into various synthesis methods have been conducted depending on novel physiological activities thereof. Particularly, in an organic phosphorus compound having a structure similar to carbon in organic compounds, chemical reactivity and physiological activity of phosphorus have been spotlighted.

Particularly, since a benzoxaphosphole 1-oxide compound, which is one of the phosphorus heterocyclic compounds, has physiological activity and may be used in synthesis of a novel medicine, it is important to develop a synthesis method thereof. Therefore, various researches for developing a synthesis method of benzoxaphosphole 1-oxide derivatives as described above have been reported (*J. Org. Chem.* 1982, 47, 1677).

In addition, a dihydro-azaphosphole 1-oxide derivative is heterocyclic compounds used as a crop protecting agent, but research into a preparation method of the dihydro-azaphosphole 1-oxide derivative has not frequently reported, and research into properties of the compound itself has not also frequently conducted, such that research into the dihydro-azaphosphole 1-oxide derivative has been demanded. As the existing reported synthesis method of a dihydro-azaphosphole 1-oxide derivative, a synthesis method using an intramolecular annulation reaction of 2-chloromethylphenylphosphinamide in the presence of 1,5-diazabicyclo-[4.3.0]non-5-ene, a synthesis method of a nucleophilic substitution reaction between multi-substituted phosphonic dichloride and a benzylamine derivative substituted with lithium, a synthesis method using a photo-decomposition process from a dimesitylenephosphinic azide derivative and an intramolecular cyclic reaction have been reported (*J. Chem. Soc., Chem. Commun.* 1991, 1187; *J. Org. Chem.* 1981, 46, 3486; U.S. Pat. No. 4,272,278A). However, in the reported synthesis methods, it is impossible to introduce a substituent at a third position of dihydro azaphosphole 1-oxide derivative, and a reaction step of introducing halide should be performed, such that these methods are uneconomical.

A synthesis method of a novel dihydro-1H-phosphole 1-oxide derivative using an olefination reaction through a carbon-hydrogen bond activation reaction of phosphonic monoester or phosphonic amide, which is a phosphonic derivative according to the related art, and a vinyl derivative and a subsequent annulation reaction has not yet been reported. Therefore, the development of a novel synthesis method of various dihydro-1H-phosphole 1-oxide derivatives using these reactions has been demanded.

SUMMARY

An embodiment of the present invention is directed to providing novel dihydro-1H-phosphole 1-oxide derivatives having pharmacological and physiological activities.

Another embodiment of the present invention is directed to providing a preparation method of novel dihydro-1H-phosphole 1-oxide derivatives.

In one general aspect, there is provided a dihydro-1H-phosphole 1-oxide derivative represented by the following Chemical Formula 1.

[Chemical Formula 1]

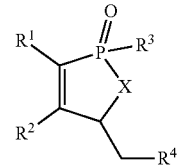

In Chemical Formula 1,

X is NR' or O;

R' is (C1-C20)alkyl or (C6-C20)aryl;

$R^1$ and $R^2$ are each independently hydrogen, (C1-C20)alkyl or (C6-C20)aryl, or are linked to each other by —$CR^{11}$=$CR^{12}$—$CR^{13}$=$CR^{14}$— to form a fused ring;

$R^{11}$ to $R^{14}$ are each independently hydrogen, (C1-C20)alkyl, halo(C1-C20)alkyl, (C1-C20)alkoxy, (C6-C20)aryl, halogen, (C1-C20)alkylcarbonyl, nitro, or (C1-C20)alkoxycarbonylethenyl, or are linked to a substituent adjacent thereto by (C1-C7)alkylene, (C2-C7)alkenylene, or (C4-C7)alkanedienylene to form a fused ring;

$R^3$ is (C1-C20)alkoxy or (C6-C20)aryl;

$R^4$ is (C1-C20)alkoxycarbonyl, (C6-C20)arylcarbonyl, (C1-C20)alkylcarbonyl, cyano, di(C1-C20)alkylcarbamoyl, di(C6-C20)arylcarbamoyl, (C6-C20)arylsulfonyl, (C1-C20)alkylsulfonyl, di(C1-C20)alkylphosphoryl, or di(C6-C20)arylphosphoryl; and alkyl and aryl of $R^1$ to $R^3$ are further substituted with one or more substituents selected from the group consisting of halogen, (C1-C20)alkyl, (C1-C20)alkoxy, and halo(C1-C20)alkyl, respectively.

In another general aspect, there is provided a preparation method of a dihydro-1H-phosphole 1-oxide derivative represented by Chemical Formula 1 characterized by performing an olefination reaction and a subsequent intermolecular annulation reaction of a phosphinic derivative represented by the following Chemical Formula 4 and a vinyl derivative represented by the following Chemical Formula 5 in the presence of a catalyst and an oxidant to prepare the dihydro-1H-phosphole 1-oxide derivative represented by Chemical Formula 1.

[Chemical Formula 4]

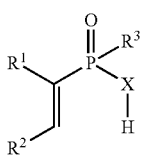

[Chemical Formula 5]

Hereinafter, the present invention will be described in detail.

Here, technical terms and scientific terms used in the present specification have the general meaning understood by those skilled in the art to which the present invention pertains unless otherwise defined. In addition, repetitive descriptions of the same technical configuration and action as those in the related art will be omitted.

The present invention provides the dihydro-1H-phosphole 1-oxide derivative represented by the following Chemical Formula 1:

[Chemical Formula 1]

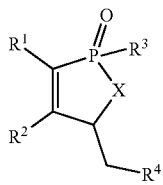

in Chemical Formula 1,
X is NR' or O;
R' is (C1-C20)alkyl or (C6-C20)aryl;
$R^1$ and $R^2$ are each independently hydrogen, (C1-C20) alkyl or (C6-C20)aryl, or are linked to each other by —$CR^{11}$=$CR^{12}$—$CR^{12}$=$CR^{14}$— to form a fused ring;
$R^{11}$ to $R^{14}$ are each independently hydrogen, (C1-C20) alkyl, halo(C1-C20)alkyl, (C1-C20)alkoxy, (C6-C20)aryl, halogen, (C1-C20)alkylcarbonyl, nitro, or (C1-C20)alkoxycarbonylethenyl, or are linked to a substituent adjacent thereto by (C1-C7)alkylene, (C2-C7)alkenylene, or (C4-C7) alkanedienylene to form a fused ring;
$R^3$ is (C1-C20)alkoxy or (C6-C20)aryl;
$R^4$ is (C1-C20)alkoxycarbonyl, (C6-C20)arylcarbonyl, (C1-C20)alkylcarbonyl, cyano, di(C1-C20)alkylcarbamoyl, di(C6-C20)arylcarbamoyl, (C6-C20)arylsulfonyl, (C1-C20) alkylsulfonyl, di(C1-C20)alkylphosphoryl, or di(C6-C20) arylphosphoryl; and
alkyl and aryl of $R^1$ to $R^3$ are further substituted with one or more substituents selected from the group consisting of halogen, (C1-C20)alkyl, (C1-C20)alkoxy, and halo(C1-C20) alkyl, respectively.

As disclosed herein, the terms [alkyl] and [alkoxy] include both of the straight chain type and the branched chain type.

As disclosed herein, the term [aryl], which is an organic radical derived from aromatic hydrocarbon by removing one hydrogen atom therefrom, includes a single ring or a fused ring containing, properly 4 to 7 ring atoms, and preferably 5 or 6 ring atoms in each ring, and include rings in which two or more aryls are combined through single bond(s). Specific examples of aryl include aromatic groups such as phenyl, naphthyl, biphenyl, indenyl, fluorenyl, phenanthryl, anthracenyl, triphenylenyl, pyrenyl, chrysenyl, and naphtacenyl.

The novel dihydro-1H-phosphole 1-oxide derivative represented by Chemical Formula 1 may include a 1,3-dihydro-1H-2,1-oxaphosphole 1-oxide derivative and a 2,3-dihydro-1H-2,1-azaphosphole 1-oxide derivative, and may be preferably represented by the following Chemical Formula 2 or 3:

[Chemical Formula 2]

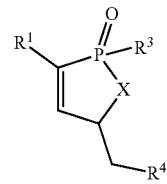

[Chemical Formula 3]

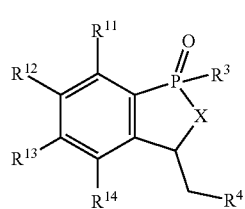

in Chemical Formulas 2 and 3, X, $R^3$, and $R^4$ have the same definitions as defined in Chemical Formula 1;
$R^1$ is (C1-C20)alkyl or (C6-C20)aryl, alkyl or aryl of $R^1$ being further substituted with one or more substituents selected from the group consisting of halogen and (C1-C20) alkyl; and
$R^{11}$ to $R^{14}$ are each independently hydrogen, (C1-C20) alkyl, halo(C1-C20)alkyl, (C1-C20)alkoxy, (C6-C20)aryl, halogen, (C1-C20)alkylcarbonyl, nitro, or (C1-C20)alkoxycarbonylethenyl, or are linked to a substituent adjacent thereto by

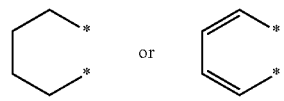 [SMILES: *CCCC* ; */C=C\C=C/*]

to form a fused ring.

More specifically, in Chemical Formulas 2 and 3, preferably, X may be NR' or O; R' is methyl, ethyl, propyl, butyl, pentyl, hexyl, phenyl, or naphthyl; $R^1$ may be methyl, ethyl, propyl, butyl, pentyl, hexyl, heptyl, octyl, phenyl, naphthyl, or fluorenyl, phenyl, naphthyl, or fluorenyl of $R^1$ being further substituted with one or more substituents selected from the group consisting of methyl, ethyl, propyl, butyl, pentyl, hexyl, trifluoromethyl, methoxy, ethoxy, propoxy, butoxy, pentyloxy, hexyloxy, chloro, bromo, fluoro, or iodo; $R^{11}$ to $R^{14}$ may be each independently hydrogen, methyl, ethyl, propyl, butyl, pentyl, hexyl, trifluoromethyl, methoxy, ethoxy, propoxy, butoxy, pentyloxy, hexyloxy, phenyl, naphthyl, fluoro, chloro, iodo, bromo, acetyl, nitro, or ethoxycarbonylethenyl, or be linked to a substituent adjacent thereto by

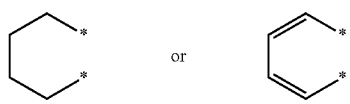 [SMILES: *CCCC* ; */C=C\C=C/*]

to form a fused ring; $R^3$ may be methoxy, ethoxy, propoxy, butoxy, pentyloxy, hexyloxy, phenyl, or naphthyl, phenyl or naphthyl of $R^3$ being further substituted with one or more substituents selected from the group consisting of methyl, ethyl, propyl, butyl, pentyl, hexyl, trifluoromethyl, methoxy, ethoxy, propoxy, butoxy, pentyloxy, hexyloxy, chloro, bromo, fluoro, or iodo; and $R^4$ may be methoxycarbonyl, ethoxycarbonyl, propoxycarbonyl, butoxycarbonyl, pentyloxycarbonyl, hexyloxycarbonyl, methylcarbonyl, ethylcarbonyl, propylcarbonyl, butylcarbonyl, pentylcarbonyl, hexylcarbonyl, cyano, dimethylcarbamoyl, diethylcarbamoyl, dipropylcarbamoyl, dibutylcarbamoyl, dipentylcarbamoyl, dihexylcarbamoyl, methylethylcarbamoyl, phenylsulfonyl, naphthylsulfonyl, dimethylphosphoryl, diethylphosphoryl, dipropylphosphoryl, dibutylphosphoryl, dipentylphosphoryl, dihexylphosphoryl, or methylethylphosphoryl.

The dihydro-1H-phosphole 1-oxide derivative according to the present invention may be selected from the following compounds, but is not limited thereto.

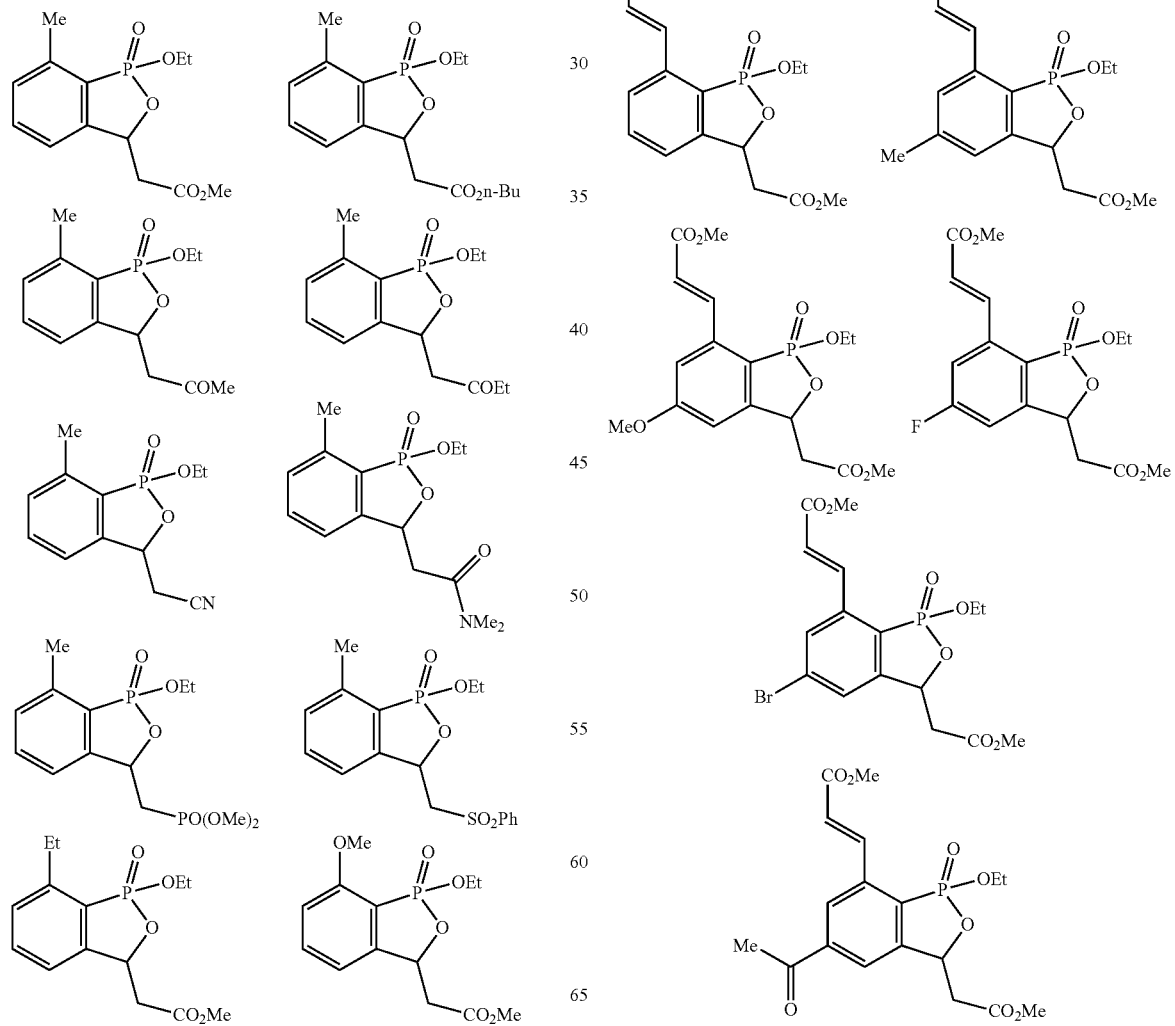

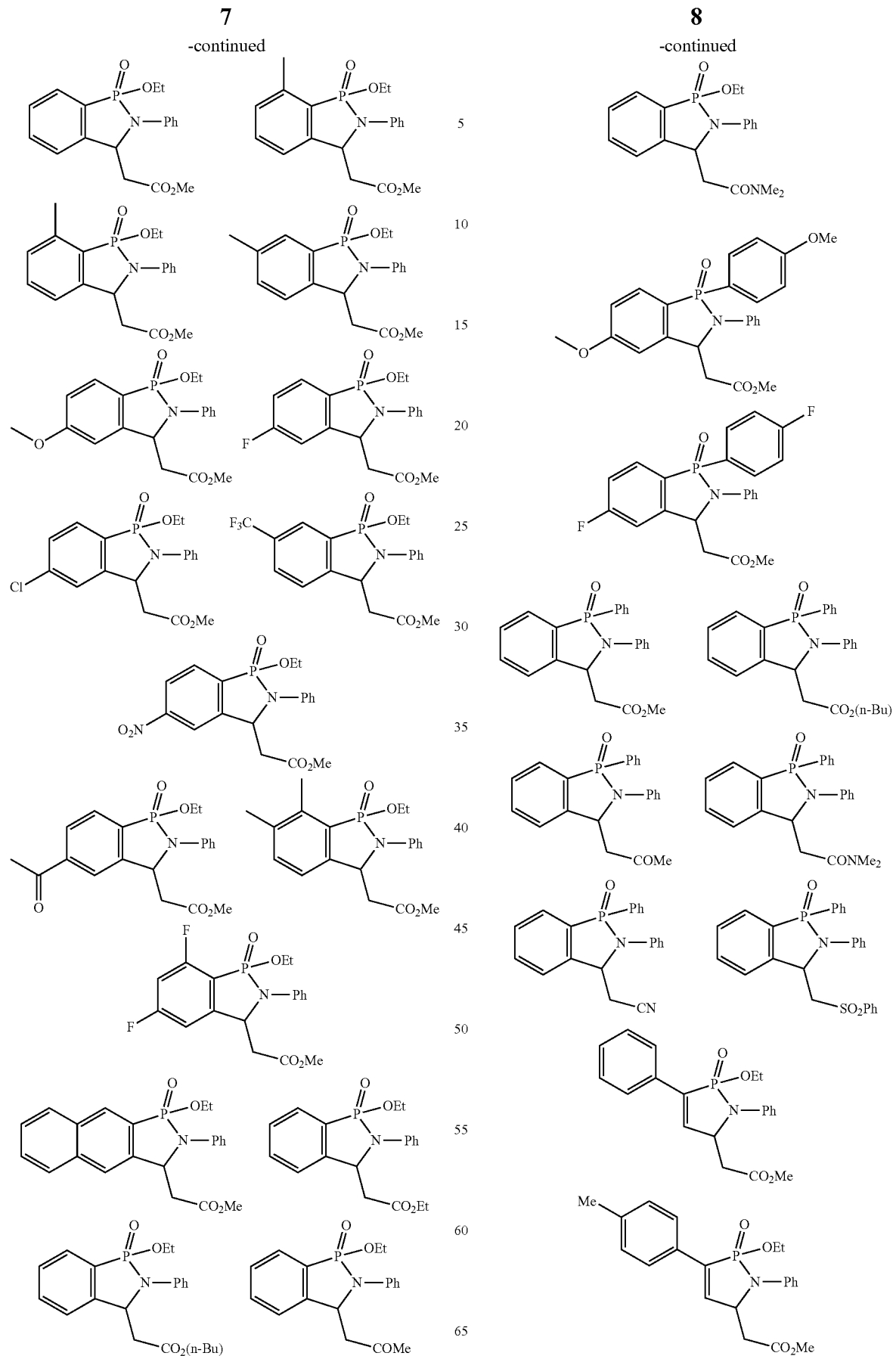

-continued

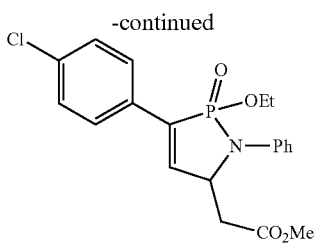

Hereinafter, the preparation method of a dihydro-1H-phosphole 1-oxide derivative according to the present invention and the preparation method thereof will be described in detail.

The present invention provides the preparation method of a dihydro-1H-phosphole 1-oxide derivative characterized by reacting the phosphinic derivative represented by the following Chemical Formula 4 and the vinyl derivative represented by the following Chemical Formula 5 with each other in the presence of a rhodium (Rh) catalyst, an oxidant, and a base to prepare the dihydro-1H-phosphole 1-oxide derivative represented by Chemical Formula 1:

[Chemical Formula 1]

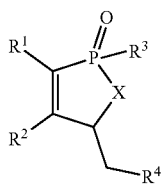

[Chemical Formula 4]

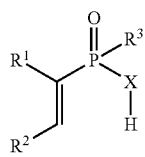

[Chemical Formula 5]

in Chemical Formulas 1, 4, and 5,

X is NR' or O;

R' is (C1-C20)alkyl or (C6-C20)aryl;

$R^1$ and $R^2$ are each independently hydrogen, (C1-C20) alkyl or (C6-C20)aryl, or are linked to each other by —$CR^{11}$=$CR^{12}$—$CR^{12}$=$CR^{14}$— to form a fused ring;

$R^{11}$ to $R^{14}$ are each independently hydrogen, (C1-C20) alkyl, halo(C1-C20)alkyl, (C1-C20)alkoxy, (C6-C20)aryl, halogen, (C1-C20)alkylcarbonyl, nitro, or (C1-C20)alkoxycarbonylethenyl, or are linked to a substituent adjacent thereto by (C1-C7)alkylene, (C2-C7)alkenylene, or (C4-C7) alkanedienylene to form a fused ring;

$R^3$ is (C1-C20)alkoxy or (C6-C20)aryl;

$R^4$ is (C1-C20)alkoxycarbonyl, (C6-C20)arylcarbonyl, (C1-C20)alkylcarbonyl, cyano, di(C1-C20)alkylcarbamoyl, di(C6-C20)arylcarbamoyl, (C6-C20)arylsulfonyl, (C1-C20) alkylsulfonyl, di(C1-C20)alkylphosphoryl, or di(C6-C20) arylphosphoryl; and alkyl and aryl of $R^1$ to $R^3$ are further substituted with one or more substituents selected from the group consisting of halogen, (C1-C20)alkyl, (C1-C20)alkoxy, and halo(C1-C20) alkyl, respectively.

The preparation method of a dihydro-1H-phosphole 1-oxide derivative represented by Chemical Formula 1 according to the present invention is a significantly effective method capable of obtaining a product with high yield and high purity by a simple process under mild conditions in the presence of the rhodium (Rh) catalyst, the oxidant, and the base.

The rhodium (Rh) catalyst used in the preparation method of a dihydro-1H-phosphole 1-oxide derivative according to the present invention may be one or a mixture of two or more selected from the group consisting of di-μ-chloro bis(1,5-cyclooctadiene)dirhodium(I) ([RhCl(cod)]$_2$), chlorobis(ethylene) rhodium(I) dimer ([RhCl(C$_2$H$_4$)$_2$]$_2$) rhodium(III) acetylacetonate (Rh(acac)$_3$), anhydrous rhodium(III) chloride (RhCl$_3$), rhodium(III) chloride hydrate (RhCl$_3$.xH$_2$O, x is an integer of 1 to 3), rhodium(III) bromide hydrate (RhBr$_3$.xH$_2$O, x is an integer of 1 to 3), rhodium(III) oxide (Rh$_2$O$_3$), rhodium(III) oxide hydrate (Rh$_2$O$_3$.xH$_2$O), tris(acetonitrile)pentamethylcyclopentadienyl rhodium(Iii) hexafluoroantimonate ([(C$_5$Me$_5$)Rh(MeCN)$_3$][SbF$_6$]$_2$), dichloro(pentamethylcyclopentadienyl)rhodium(III) dimer ([Rh(C$_5$Me$_5$)Cl$_2$]$_2$), trichlorotris(ethylenediamine) rhodium (III) trihydrate ((H$_2$NCH$_2$CH$_2$NH$_2$)$_3$RhCl$_3$.3H$_2$O), chlorobis (2-phenylpyridine)rhodium(III) dimer, dichloro(dimethylglyoximato) (dimethylglyoxime)rhodium(III), trichloro-[1,1, 1-tri(diphenylphosphinomethyl)ethane]rhodium(III), rhodium(III) iodide (RhI$_3$), rhodium(III) 2,4-pentanedionate, and rhodium(III) sulfate tetrahydrate (Rh$_2$(SO$_4$)$_3$.4H$_2$O). Preferably, [Rh(C$_5$Me$_5$)Cl$_2$]$_2$ may be used as the rhodium (Rh) catalyst.

The rhodium (Rh) catalyst used in the preparation method of a dihydro-1H-phosphole 1-oxide derivative according to the present invention may be used in a range of 0.01 to 0.2 equivalents, with respect to the phosphinic derivative represented by the Chemical Formula 4. It is more preferable that 0.04 equivalents of the rhodium (Rh) derivative is used. In the case of using the rhodium (Rh) catalyst in the above-mentioned range, the dihydro-1H-phosphole 1-oxide derivative may be prepared with high yield, and in the case in which an amount of the rhodium (Rh) catalyst is out of the range, yield and economic efficiency may be deteriorated.

As the oxidant used in the preparation method of a dihydro-1H-phosphole 1-oxide derivative according to the present invention, one or a mixture of two or more selected from the group consisting of silver (I) oxide (Ag$_2$O), sliver (II) oxide (Ago), silver acetate (AgOAc), silver (I) carbonate (Ag$_2$CO$_3$), silver hexafluoroantimonate (V) (AgSbF$_6$), silver triflate (AgOTf), copper (II) acetate monohydrate (Cu (OAc)$_2$.H$_2$O), copper(I) chloride (CuCl), copper(II) oxide (CuO), copper(I) oxide (Cu$_2$O), copper(I) acetate (CuOAc), copper(II) acetate (Cu(OAc)$_2$), copper triflate (Cu(OTf)$_2$), sodium persulfate (Na$_2$S$_2$O$_8$), potassium persulfate (K$_2$S$_2$O$_2$), ammonium persulfate (NH$_4$)$_2$S$_2$O$_8$), oxygen, 2,2, 6,6-tetramethyl-1-piperidinyloxy(free radical) (TEMPO), sodium acetate (NaOAc), p-benzoquinone, N-iodosuccinimide (NIS), N-chlorosuccinimide (NCS), N-bromosuccinimide (NBS), iron chloride (FeCl$_3$), manganese (III) acetate dihydrate (Mn(OAc)$_3$.2H$_2$O), vanadium (V) bis(trifluoroacetoxy)iodobenzene (PhI(TFA)$_2$), acetyl hypoiodite (IOAc), and ozone may be used. In view of reactivity and yield, it is most preferable that AgOAc, Cu(OAc)$_2$, TEMPO or a mixture thereof is used as the oxidant.

The oxidant used in the preparation method of a dihydro-1H-phosphole 1-oxide derivative according to the present invention may be used in a range of 0.5 to 3.0 equivalents, with respect to the phosphinic derivative represented by the Chemical Formula 4, and it is preferable that 1.0 to 2.0 equivalents of the oxidant is used. Only in the case of using the oxidant in the range of 0.5 to 3.0 equivalents, the dihydro-1H-phosphole 1-oxide derivative may be prepared with high yield, and in the case in which an amount of oxidant is out of the range, yield and economic efficiency may be deteriorated.

The base used in the preparation method of a dihydro-1H-phosphole 1-oxide derivative according to the present invention may be one or a mixture of two or more selected from the group consisting of cesium fluoride [CsF], cesium pivalate [$(CH_2)_2CCOOCs$], cesium acetate [$CH_2COOCs$], lithium acetate [LiOAc], potassium acetate [$CH_3COOK$], sodium acetate [NaOAc], cesium carbonate [$Cs_2CO_3$], lithium carbonate [$Li_2CO_2$], sodium carbonate [$Na_2CO_2$], potassium carbonate [$K_2CO_3$], potassium phosphate monobasic [$KH_2PO_4$], potassium phosphate dibasic [$K_2HPO_4$], potassium phosphate tribasic [$K_2PO_4$], sodium phosphate dibasic dihydrate [$Na_2HPO_4\cdot2H_2O$], sodium phosphate dibasic [$Na_2HPO_4$], and sodium phosphate monobasic [$NaH_2PO_4$]. Preferably, cesium pivalate [$(CH_3)_3CCOOCs$], cesium carbonate [$Cs_2CO_3$], sodium phosphate dibasic [$Na_2HPO_4$], or a mixture thereof may be used as the base. The base used in the preparation method of a dihydro-1H-phosphole 1-oxide derivative according to the present invention may be used in a range of 0.5 to 3.0 equivalents, with respect to the phosphinic derivative represented by the Chemical Formula 4, and preferably, 0.75 to 2.0 equivalents of the base may be used. Only in the case of using the base in the range of 0.5 to 3.0 equivalents, the dihydro-1H-phosphole 1-oxide derivative may be prepared with high yield, and in the case in which an amount of the base is out of the range, yield and economic efficiency may be deteriorated.

The vinyl derivative represented by Chemical Formula 5 used in the preparation method of a dihydro-1H-phosphole 1-oxide derivative according to the present invention may be used in a range of 1.0 to 3.0 equivalents with respect to the phosphinic derivative represented by Chemical Formula 4, and in view of yield and economic efficiency, it is most preferable that 2.0 to 3.0 equivalents of the vinyl derivative is used.

As a solvent used in the preparation method of a dihydro-1H-phosphole 1-oxide derivative according to the present invention, any solvent may be used as long as it is generally used, but it is preferable that 1,4-dioxane, dichloromethane (DCM), dichloroethane (DCE), toluene, benzene, trifluoromethylbenzene, xylene, acetonitrile (MeCN), nitromethane, tetrahydrofuran (THF), N,N-dimethylformamide (DMF), acetamide, mesitylene, chlorobenzene, hexafluorobenzene, octafluorotoluene, pivalic acid, N,N-dimethylacetamide (DMA), methanol, ethanol, tert-amyl alcohol, tert-butyl alcohol, or a mixed solvent thereof is used. More preferably, dichloroethane (DCE), xylene, or acetonitrile (MeCN) may be used.

In the preparation method of a dihydro-1H-phosphole 1-oxide derivative according to the present invention, any reaction temperature may be possible as long as it is a general temperature used in organic synthesis. However, the reaction temperature may be changed depending on a reaction time and amounts of a reactant and a starting material, and in order to prevent the reaction time from being increased or a reaction yield from being deteriorated by generation of by-products, an annulation reaction may be performed in a temperature range of room temperature to 15° C., and preferably 80 to 110° C.

The reaction time may be changed depending on the reactant, the amount of the reactant, and the kind and amount of solvent, and the reaction is terminated after confirming that the phosphinic derivative represented by Chemical Formula 4, which is the starting material, is completely consumed using thin layer chromatography (TLC), or the like. When the reaction is completed, after distilling the solvent under reduced pressure, a target material may be separated and purified by a general method such as column chromatography, or the like.

DETAILED DESCRIPTION OF EMBODIMENTS

Hereinafter, configurations of the present invention will be described in more detail through the Examples, but the following Examples are only to assist in understanding of the present invention. Therefore, the scope of the present invention is not limited thereto.

Example 1

Preparation of Methyl 2-(1-ethoxy-7-methyl-1,3-dihydrobenzo[c][1,2]oxaphosphol-3-yl-1-oxide)acetate

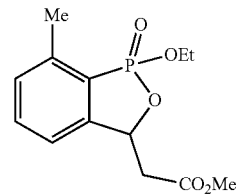

After putting dichloro(pentamethylcyclopentadienyl) rhodium(III) dimer ([$Rh(C5Me_5)Cl_2]_2$, 4.94 mg, 0.04 eq, 4 mol %), AgOAc (66.8 mg, 0.4 mmol), and $Na_2HPO_4$ (28.4 mg, 0.2 mmol) into a reaction V-vial (diameter: 2 cm, height: 4 cm) in a glove box, 2-methylphenylphosphonic monoethyl ester (40.0 mg, 0.2 mmol), methyl acrylate (34.0 mg, 0.4 mmol), and $CH_3CN$ (2.0 mL) were added thereto and stirred at 110° C. for 16 hours. After confirming that the starting material was completely consumed using TLC, the resultant was extracted with $CH_2Cl_2$ and the reaction was terminated by celite filtration. An extracted organic layer was dried over anhydrous magnesium sulfate and filtered. After removing the solvent, the resultant was separated using column chromatography, thereby obtaining methyl 2-(1-ethoxy-7-methyl-1,3-dihydrobenzo[c][1,2]oxaphosphol-3-yl-1-oxide)acetate (48.2 mg, 85%) corresponding to the target compound.

$^1$H NMR (400 MHz, $CDCl_3$) δ 7.49 (tdd, J=7.6, 3.6, 0.9 Hz, 1H), 7.29-7.25 (m, 1H), 7.12 (dd, J=7.6, 2.1 Hz, 1H), 5.85-5.76 (m, 1H), 4.29-4.05 (m, 2H), 3.76 (s, 3H), 2.91-2.86 (m, 2H), 2.59 (s, 3H), 1.34 (t, J=7.1 Hz, 3H)

Example 2

Preparation of n-Butyl 2-(1-ethoxy-7-methyl-1,3-dihydrobenzo[c][1,2]oxaphosphol-3-yl-1-oxide)acetate

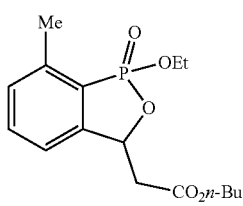

A reaction was performed by the same method as in Example 1 except for using n-butyl acrylate (51.3 mg, 0.4 mmol) instead of methyl acrylate of Example 1, thereby obtaining n-butyl 2-(1-ethoxy-7-methyl-1,3-dihydrobenzo[c][1,2]oxaphosphol-3-yl-1-oxide)acetate (56.5 mg, 87%) corresponding to the target compound.

$^1$H NMR (400 MHz, CDCl$_3$) δ 7.49 (t, J=7.4 Hz, 1H), 7.26 (t, J=7.3 Hz, 1H), 7.13 (dd, J=7.7, 2.5 Hz, 1H), 5.80 (td, J=13.2, 4.8 Hz, 1H), 4.28-4.11 (m, 4H), 2.88 (dd, J=15.6, 4.8 Hz, 1H), 2.77 (dd, J=15.6, 8.5 Hz, 1H), 2.58 (s, 3H), 1.67-1.60 (m, 2H), 1.41-1.35 (m, 2H), 1.38 (t, J=7.1 Hz, 3H), 0.94 (t, J=7.4 Hz, 3H)

Example 3

Preparation of 1-(1-Ethoxy-7-methyl-1,3-dihydrobenzo[c][1,2]oxaphosphol-3-yl-1-oxide)propan-2-one

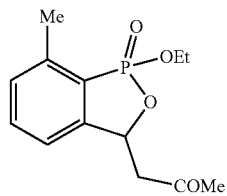

A reaction was performed by the same method as in Example 1 except for using methyl vinyl ketone (28.0 mg, 0.4 mmol) instead of methyl acrylate of Example 1, thereby obtaining 1-(1-ethoxy-7-methyl-1,3-dihydrobenzo[c][1,2]oxaphosphol-3-yl-1-oxide)propan-2-one (41.8 mg, 78%) corresponding to the target compound.

$^1$H NMR (400 MHz, CDCl$_3$) δ 7.47 (td, J=11.5, 1.0 Hz, 1H), 7.26 (t, J=6.9 Hz, 1H), 7.10 (dd, J=7.7, 2.4 Hz, 1H), 5.82 (dt, J=11.7, 3.8 Hz, 1H), 4.22-4.02 (m, 2H), 3.10 (dd, J=17.0, 8.3 Hz, 1H), 2.91 (dd, J=17.0, 4.2 Hz, 1H), 2.58 (s, 3H), 2.27 (s, 3H), 1.33 (t, J=7.1 Hz, 3H)

Example 4

Preparation of 1-(1-Ethoxy-7-methyl-1,3-dihydrobenzo[c][1,2]oxaphosphol-3-yl-1-oxide)butan-2-one

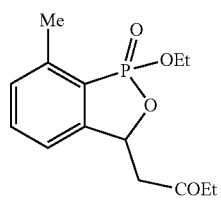

A reaction was performed by the same method as in Example 1 except for using ethyl vinyl ketone (33.6 mg, 0.4 mmol) instead of methyl acrylate of Example 1, thereby obtaining 1-(1-ethoxy-7-methyl-1,3-dihydrobenzo[c][1,2]oxaphosphol-3-yl-1-oxide)butan-2-one (41.8 mg, 74%) corresponding to the target compound.

$^1$H NMR (400 MHz, CDCl$_3$) δ 7.48 (td, J=8.2, 1.1 Hz, 1H), 7.27-7.23 (m, 1H), 7.11-7.07 (m, 1H), 5.88-5.81 (m, 1H), 4.30-4.02 (m, 2H), 3.07 (dd, J=16.7, 8.4 Hz, 1H), 2.87 (dd, J=16.7, 3.8 Hz, 1H), 2.58 (s, 3H), 2.58-2.45 (m, 2H), 1.33 (t, J=7.1 Hz, 3H), 1.11 (t, J=7.3 Hz, 3H)

Example 5

Preparation of 2-(1-Ethoxy-7-methyl-1,3-dihydrobenzo[c][1,2]oxaphosphol-3-yl-1-oxide)acetonitrile

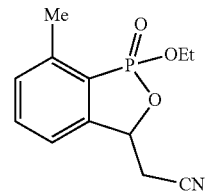 [SMILES: CCOP1(=O)OC(CC#N)c2cccc(C)c21]

A reaction was performed by the same method as in Example 1 except for using acrylonitrile (21.2 mg, 0.4 mmol) instead of methyl acrylate of Example 1, thereby obtaining 2-(1-Ethoxy-7-methyl-1,3-dihydrobenzo[c][1,2]oxaphosphol-3-yl-1-oxide)acetonitrile (45.4 mg, 90%) corresponding to the target compound.

¹H NMR (400 MHz, CDCl₃) δ 7.56 (td, J=11.5, 1.1 Hz, 1H), 7.36-7.30 (m, 2H), 5.53 (q, J=6.4 Hz, 1H), 4.27-4.15 (m, 2H), 3.02-2.91 (m, 2H), 2.60 (s, 3H), 1.37 (t, J=7.1 Hz, 3H)

Example 6

Preparation of 2-(1-Ethoxy-7-methyl-1,3-dihydrobenzo[c][1,2]oxaphosphol-3-yl-1-oxide)-N,N-dimethylacetamide

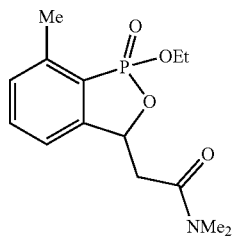 [SMILES: CCOP1(=O)OC(CC(=O)N(C)C)c2cccc(C)c21]

A reaction was performed by the same method as in Example 1 except for using N,N-dimethylacrylamide (39.7 mg, 0.4 mmol) instead of methyl acrylate of Example 1, thereby obtaining 2-(1-ethoxy-7-methyl-1,3-dihydrobenzo[c][1,2]oxaphosphol-3-yl-1-oxide)-N,N-dimethylacetamide (42.2 mg, 71%) corresponding to the target compound.

¹H NMR (400 MHz, CDCl₃) δ 7.51-7.45 (m, 1H), 7.28-7.21 (m, 2H), 5.97-5.91 (m, 1H), 4.19-3.97 (m, 2H), 3.06-2.94 (m, 1H), 3.03 (s, 3H), 3.01 (s, 3H), 2.78-2.72 (m, 1H), 2.58 (s, 3H), 1.38 (t, J=7.1 Hz, 3H)

Example 7

Preparation of dimethyl(1-Ethoxy-7-methyl-1,3-dihydrobenzo[c][1,2]oxaphosphol-3-yl-1-oxide)methylphosphonate

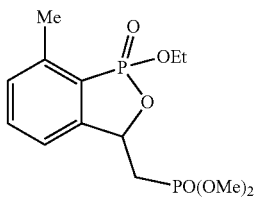

A reaction was performed by the same method as in Example 1 except for using dimethyl vinylphosphonate (81.7 mg, 0.6 mm) instead of methyl acrylate of Example 1, thereby obtaining dimethyl(1-ethoxy-7-methyl-1,3-dihydrobenzo[c][1,2]oxaphosphol-3-yl-1-oxide)methylphosphonate (40.8 mg, 61%) corresponding to the target compound.

¹H NMR (400 MHz, CDCl₃) δ 7.50 (tdd, J=11.4, 3.4, 1.1 Hz, 1H), 7.29-7.25 (m, 1H), 7.18 (td, J=8.6, 2.5 Hz, 1H), 5.75-5.64 (m, 1H), 4.30-4.04 (m, 2H), 3.89 (d, J=3.5 Hz, 3H), 3.86 (d, J=3.4 Hz, 3H), 2.59 (s, 3H), 2.48-2.16 (m, 2H), 1.39 (t, J=7.1 Hz, 3H)

Example 8

Preparation of 1-Ethoxy-7-methyl-3-(phenylsulfonylmethyl)-1,3-dihydrobenzo[c][1,2]oxaphosphole-1-oxide

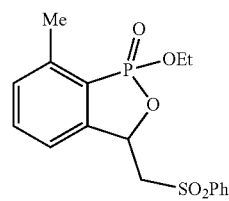

A reaction was performed by the same method as in Example 1 except for using phenyl vinyl sulfone (101.0 mg, 0.6 mmol) instead of methyl acrylate of Example 1, thereby obtaining 1-ethoxy-7-methyl-3-(phenylsulfonylmethyl)-1,3-dihydrobenzo[c][1,2]oxaphosphole-1-oxide (52.0 mg, 71%) corresponding to the target compound.

¹H NMR (400 MHz, CDCl₃) δ 8.05-8.03 (m, 2H), 7.72-7.68 (m, 1H), 7.63-7.59 (m, 2H), 7.51 (td, J=11.5, 1.2 Hz, 1H), 7.26 (td, J=10.4, 0.7 Hz, 1H), 7.16 (ddd, J=7.8, 2.9, 0.6 Hz, 1H), 5.86 (td, J=11.2, 2.4 Hz, 1H), 4.04-3.94 (m, 1H), 3.87-3.77 (m, 1H), 3.59 (dd, J=15.1, 2.2 Hz, 1H), 3.47 (dd, J=15.1, 9.7 Hz, 1H), 2.52 (s, 3H), 1.13 (t, J=7.1 Hz, 3H)

Example 9

Preparation of Methyl 2-(1-ethoxy-7-ethyl-1,3-dihydrobenzo[c][1,2]oxaphosphol-3-yl-1-oxide)acetate

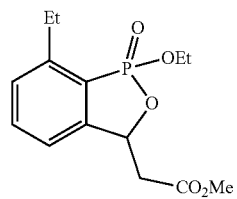

A reaction was performed by the same method as in Example 1 except for using 2-ethylphenyl phosphonic monoethyl ester (42.8 mg, 0.2 mmol) instead of 2-methylphenylphosphonic monoethyl ester of Example 1, thereby obtaining methyl 2-(1-ethoxy-7-ethyl-1,3-dihydrobenzo[c][1,2]oxaphosphol-3-yl-1-oxide)acetate (53.0 mg, 89%) corresponding to the target compound.

¹H NMR (400 MHz, CDCl₃) δ 7.53 (td, J=11.5, 1.2 Hz, 1H), 7.34-7.30 (m, 1H), 7.13 (dd, J=7.7, 2.7 Hz, 1H), 5.85-

5.76 (m, 1H), 4.28-4.05 (m, 2H), 3.77 (s, 3H), 2.97-2.90 (m, 2H), 2.92-2.87 (m, 2H), 1.34 (t, J=7.3 Hz, 3H), 1.33 (t, J=7.6 Hz, 3H)

Example 10

Preparation of Methyl 2-(1-ethoxy-7-methoxy-1,3-dihydrobenzo[c][1,2]oxaphosphol-3-yl-1-oxide)acetate

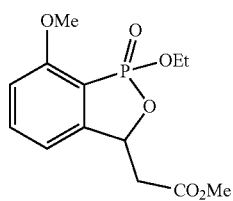

A reaction was performed by the same method as in Example 1 except for using 2-methoxyphenyl phosphonic monoethyl ester (43.2 mg, 0.2 mmol) instead of 2-methylphenylphosphonic monoethyl ester of Example 1, thereby obtaining methyl 2-(1-ethoxy-7-methoxy-1,3-dihydrobenzo[c][1,2]oxaphosphol-3-yl-1-oxide)acetate (51.0 mg, 85%) corresponding to the target compound.

$^1$H NMR (400 MHz, CDCl$_3$) δ 7.55 (tdd, J=8.0, 3.3, 0.7 Hz, 1H), 6.91-6.85 (m, 2H), 5.82-5.73 (m, 1H), 4.34-4.17 (m, 2H), 3.94 (s, 3H), 3.77 (s, 3H), 2.91-2.84 (m, 1H), 2.79 (dd, J=15.9, 8.2 Hz, 1H), 1.35 (t, J=7.1 Hz, 3H)

Example 11

Preparation of Methyl 2-(1-ethoxy-7-phenyl-1,3-dihydrobenzo[c][1,2]oxaphosphol-3-yl-1-oxide)acetate

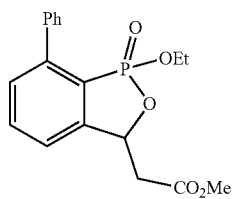 [SMILES: CCOP1(=O)OC(CC(=O)OC)c2cccc(CC)c21]

A reaction was performed by the same method as in Example 1 except for using 2-biphenylphosphonic monoethyl ester (52.5 mg, 0.2 mmol) instead of 2-methylphenylphosphonic monoethyl ester of Example 1, thereby obtaining methyl 2-(1-ethoxy-7-phenyl-1,3-dihydrobenzo[c][1,2]oxaphosphol-3-yl-1-oxide)acetate (68.0 mg, 98%) corresponding to the target compound.

$^1$H NMR (400 MHz, CDCl$_3$) δ 7.75-7.72 (m, 2H), 7.65 (td, J=11.5, 1.2 Hz, 1H), 7.51-7.40 (m, 4H), 7.30 (dd, J=7.8, 2.6 Hz, 1H), 5.81 (q, J=6.8 Hz, 1H), 3.96-3.77 (m, 2H), 3.78 (s, 3H), 3.00 (d, J=6.5 Hz, 2H), 0.99 (t, J=7.1 Hz, 3H)

Example 12

Preparation of Methyl 2-(1-ethoxy-7-chloro-1,3-dihydrobenzo[c][1,2]oxaphosphol-3-yl-1-oxide)acetate

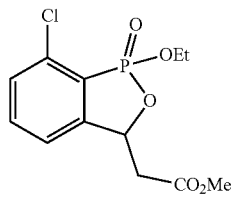

A reaction was performed by the same method as in Example 1 except for using 2-chlorophenyl phosphonic monoethyl ester (44.1 mg, 0.2 mmol) instead of 2-methylphenylphosphonic monoethyl ester of Example 1, thereby obtaining methyl 2-(1-ethoxy-7-chloro-1,3-dihydrobenzo[c][1,2]oxaphosphol-3-yl-1-oxide)acetate (48.0 mg, 80%) corresponding to the target compound.

$^1$H NMR (400 MHz, CDCl$_3$) δ 7.54 (td, J=11.7, 1.0 Hz, 1H), 7.45 (dd, J=7.9, 5.9 Hz, 1H), 7.24 (dd, J=7.7, 2.2 Hz, 1H), 5.79 (q, J=6.8 Hz, 1H), 4.37-4.26 (m, 2H), 3.77 (s, 3H), 2.94-2.92 (m, 2H), 1.38 (td, J=7.1, 0.4 Hz, 3H)

Example 13

Preparation of Methyl 2-(1-ethoxy-6,7-dimethyl-1,3-dihydrobenzo[c][1,2]oxaphosphol-3-yl-1-oxide)acetate

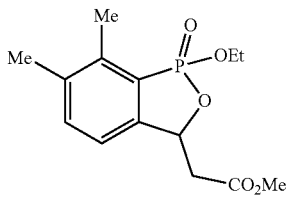 [SMILES: CCOP1(=O)OC(CC(=O)OC)c2ccc(C)c(C)c21]

A reaction was performed by the same method as in Example 1 except for using 2,3-dimethylphenyl phosphonic monoethyl ester (42.8 mg, 0.2 mmol) instead of 2-methylphenylphosphonic monoethyl ester of Example 1, thereby obtaining methyl 2-(1-ethoxy-6,7-dimethyl-1,3-dihydrobenzo[c][1,2]oxaphosphol-3-yl-1-oxide)acetate (53.6 mg, 90%) corresponding to the target compound.

major: $^1$H NMR (400 MHz, CDCl$_3$) δ 7.36 (dd, J=7.8, 2.9 Hz, 1H), 7.02 (dd, J=7.8, 3.2 Hz, 1H), 5.80-5.71 (m, 1H), 4.27-4.03 (m, 2H), 3.76 (s, 3H), 2.88 (d, J=6.4 Hz, 2H), 2.49 (s, 3H), 2.32 (s, 3H), 1.33 (t, J=7.1 Hz, 3H)

Example 14

Preparation of Methyl 2-(1-ethoxy-4,7-dimethyl-1,3-dihydrobenzo[c][1,2]oxaphosphol-3-yl-1-oxide)acetate

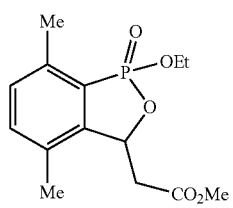 [SMILES: CCOP1(=O)OC(CC(=O)OC)c2c(C)ccc(C)c21]

A reaction was performed by the same method as in Example 1 except for using 2,5-dimethylphenyl phosphonic monoethyl ester (42.8 mg, 0.2 mmol) instead of 2-methylphenylphosphonic monoethyl ester of Example 1, thereby obtaining methyl 2-(1-ethoxy-4,7-dimethyl-1,3-dihydrobenzo[c][1,2]oxaphosphol-3-yl-1-oxide)acetate (20.9 mg, 35%) corresponding to the target compound.

$^1$H NMR (400 MHz, CDCl$_3$) δ 7.29-7.27 (m, 1H), 7.20-7.15 (m, 1H), 5.86-5.78 (m, 1H), 4.16-3.98 (m, 2H), 3.77 (s, 3H), 3.04-2.96 (m, 1H), 2.70 (dd, J=16.6, 9.9 Hz, 1H), 2.54 (s, 3H), 2.28 (s, 3H), 1.31 (t, J=7.1 Hz, 3H)

Example 15

Preparation of Methyl 2-(1-ethoxy-5-methoxy-7-methyl-1,3-dihydrobenzo[c][1,2]oxaphosphol-3-yl-1-oxide)acetate

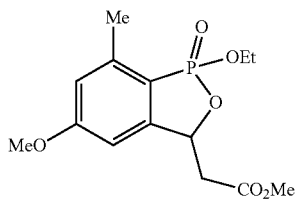 [SMILES: CCOP1(=O)OC(CC(=O)OC)c2cc(OC)cc(C)c21]

A reaction was performed by the same method as in Example 1 except for using 4-methoxy-2-methylphenyl phosphonic monoethyl ester (46.0 mg, 0.2 mmol) instead of 2-methylphenylphosphonic monoethyl ester of Example 1, thereby obtaining methyl 2-(1-ethoxy-5-methoxy-7-methyl-1,3-dihydrobenzo[c][1,2]oxaphosphol-3-yl-1-oxide)acetate (54.0 mg, 86%) corresponding to the target compound.

$^1$H NMR (400 MHz, CDCl$_3$) δ 6.79 (s, 1H), 6.58 (s, 1H), 5.78-5.69 (m, 1H), 4.26-4.00 (m, 2H), 3.84 (s, 3H), 3.77 (s, 3H), 2.90-2.84 (m, 2H), 2.54 (s, 3H), 1.33 (t, J=7.2 Hz, 3H)

Example 16

Preparation of Methyl 2-(1-ethoxy-1,3-dihydronaphtho[1,2-c][1,2]oxaphosphol-3-yl-1-oxide)acetate

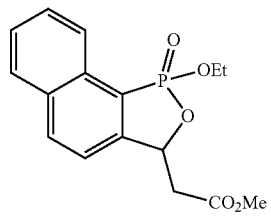 [SMILES: CCOP1(=O)OC(CC(=O)OC)c2ccc3ccccc3c21]

A reaction was performed by the same method as in Example 1 except for using 1-naphthyl phosphonic monoethyl ester (47.2 mg, 0.2 mmol) instead of 2-methylphenylphosphonic monoethyl ester of Example 1, thereby obtaining methyl 2-(1-ethoxy-1,3-dihydronaphtho[1,2-c][1,2]oxaphosphol-3-yl-1-oxide)acetate corresponding to the target compound.

$^1$H NMR (400 MHz, CDCl$_3$) δ 8.24-8.20 (m, 1H), 8.08 (dd, J=8.5, 3.0 Hz, 1H), 7.96 (dd, J=8.0, 1.2 Hz, 1H), 7.69 (t, J=7.5 Hz, 1H), 7.65-7.61 (m, 1H), 7.36 (dd, J=8.5, 2.7 Hz, 1H), 6.00-5.93 (m, 1H), 4.36-4.09 (m, 2H), 3.79 (s, 3H), 3.06-2.93 (m, 2H), 1.33 (t, J=7.1 Hz, 3H)

Example 17

Preparation of (E)-Methyl 3-(1-ethoxy-3-(2-methoxy-2-oxoethyl)-1,3-dihydrobenzo[c][1,2]oxaphosphol-7-yl-1-oxide)acrylate

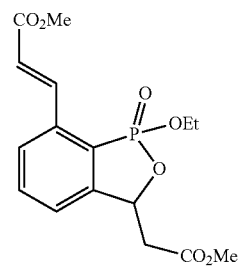 [SMILES: CCOP1(=O)OC(CC(=O)OC)c2cccc(/C=C/C(=O)OC)c21]

A reaction was performed by the same method as in Example 1 except for using phenyl phosphonic monoethyl ester (37.2 mg, 0.2 mmol) instead of 2-methylphenylphosphonic monoethyl ester of Example 1, thereby obtaining (E)-Methyl 3-(1-ethoxy-3-(2-methoxy-2-oxoethyl)-1,3-dihydrobenzo[c][1,2]oxaphosphol-7-yl-1-oxide)acrylate (54.0 mg, 76%) corresponding to the target compound.

$^1$H NMR (400 MHz, CDCl$_3$) δ 7.94 (d, J=16.1 Hz, 1H), 7.71-7.61 (m, 2H), 7.33 (dd, J=7.5, 2.2 Hz, 1H), 6.72 (d,

J=16.1 Hz, 1H), 5.88-5.79 (m, 1H), 4.35-4.15 (m, 2H), 3.82 (s, 3H), 3.78 (s, 3H), 2.94 (d, J=6.5 Hz, 2H), 1.35 (t, J=7.0 Hz, 3H)

Example 18

Preparation of (E)-Methyl 3-(1-ethoxy-5-methyl-3-(2-methoxy-2-oxoethyl)-1,3-dihydrobenzo[c][1,2]oxaphosphol-7-yl-1-oxide)acrylate

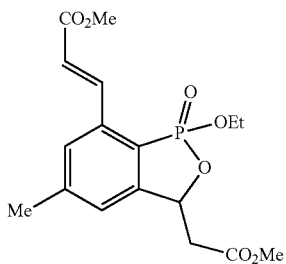 [SMILES: CCOP1(=O)OC(CC(=O)OC)c2cc(C)cc(/C=C/C(=O)OC)c21]

A reaction was performed by the same method as in Example 1 except for using 4-methylphenyl phosphonic monoethyl ester (40.0 mg, 0.2 mmol) instead of 2-methylphenylphosphonic monoethyl ester of Example 1, thereby obtaining (E)-methyl 3-(1-ethoxy-5-methyl-3-(2-methoxy-2-oxoethyl)-1,3-dihydrobenzo[c][1,2]oxaphosphol-7-yl-1-oxide)acrylate (55.2 mg, 75%) corresponding to the target compound.

$^1$H NMR (400 MHz, CDCl$_3$) δ 7.90 (dd, J=16.1, 0.9 Hz, 1H), 7.49-7.47 (m, 1H), 7.11 (s, 1H), 6.71 (dd, J=16.0, 3.6 Hz, 1H), 5.84-5.74 (m, 1H), 4.29-4.11 (m, 2H), 3.81 (d, J=0.6 Hz, 3H), 3.78 (s, 3H), 2.93-2.87 (m, 2H), 2.46 (s, 3H), 1.33 (t, J=7.2 Hz, 3H)

Example 19

Preparation of (E)-Methyl 3-(1-ethoxy-5-methoxy-3-(2-methoxy-2-oxoethyl)-1,3-dihydrobenzo[c][1,2]oxaphosphol-7-yl-1-oxide)acrylate

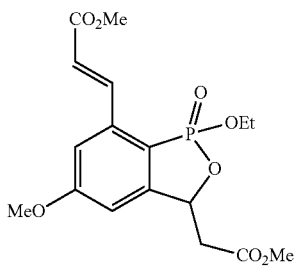 [SMILES: CCOP1(=O)OC(CC(=O)OC)c2cc(OC)cc(/C=C/C(=O)OC)c21]

A reaction was performed by the same method as in Example 1 except for using 4-methoxylphenyl phosphonic monoethyl ester (43.2 mg, 0.2 mmol) instead of 2-methylphenylphosphonic monoethyl ester of Example 1, thereby obtaining (E)-methyl 3-(1-ethoxy-5-methoxy-3-(2-methoxy-2-oxoethyl)-1,3-dihydrobenzo[c][1,2]oxaphosphol-7-yl-1-oxide)acrylate (59.2 mg, 77%) corresponding to the target compound.

$^1$H NMR (400 MHz, CDCl$_3$) δ 7.86 (d, J=16.0 Hz, 1H), 7.16 (s, 1H), 6.79 (s, 1H), 6.70 (dd, J=16.0, 4.0 Hz, 1H), 5.82-5.73 (m, 1H), 4.31-4.10 (m, 2H), 3.88 (s, 3H), 3.82 (s, 3H), 3.78 (s, 3H), 2.95-2.86 (m, 2H), 1.33 (t, J=7.2 Hz, 3H)

Example 20

Preparation of (E)-Methyl 3-(1-ethoxy-5-fluoro-3-(2-methoxy-2-oxoethyl)-1,3-dihydrobenzo[c][1,2]oxaphosphol-7-yl-1-oxide)acrylate

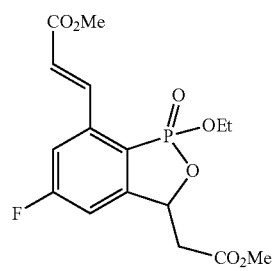 [SMILES: CCOP1(=O)OC(CC(=O)OC)c2cc(F)cc(/C=C/C(=O)OC)c21]

A reaction was performed by the same method as in Example 1 except for using 4-fluorophenyl phosphonic monoethyl ester (41.0 mg, 0.2 mmol) instead of 2-methylphenylphosphonic monoethyl ester of Example 1, thereby obtaining (E)-methyl 3-(1-ethoxy-5-fluoro-3-(2-methoxy-2-oxoethyl)-1,3-dihydrobenzo[c][1,2]oxaphosphol-7-yl-1-oxide)acrylate (48.4 mg, 65%) corresponding to the target compound.

$^1$H NMR (400 MHz, CDCl$_3$) δ 7.88 (d, J=16.0 Hz, 1H), 7.39-7.35 (m, 1H), 7.04 (d, J=7.9 Hz, 1H), 6.68 (dd, J=16.0, 3.6 Hz, 1H), 5.84-5.75 (m, 1H), 4.36-4.17 (m, 2H), 3.83 (s, 3H), 3.78 (s, 3H), 2.99 (dd, J=16.7, 7.6 Hz, 1H), 2.94-2.87 (m, 1H), 1.36 (t, J=7.1 Hz, 3H)

Example 21

Preparation of (E)-Methyl 3-(1-ethoxy-5-acetyl-3-(2-methoxy-2-oxoethyl)-1,3-dihydrobenzo[c][1,2]oxaphosphol-7-yl-1-oxide)acrylate

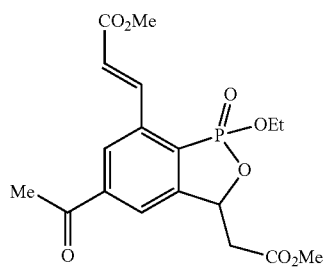

A reaction was performed by the same method as in Example 1 except for using 4-acetylphenyl phosphonic monoethyl ester (45.6 mg, 0.2 mmol) instead of 2-methylphenylphosphonic monoethyl ester of Example 1, thereby obtaining (E)-methyl 3-(1-ethoxy-5-acetyl-3-(2-methoxy-2-oxoethyl)-1,3-dihydrobenzo[c][1,2]oxaphosphol-7-yl-1-oxide)acrylate (52.3 mg, 66%) corresponding to the target compound.

$^1$H NMR (400 MHz, CDCl$_3$) δ 8.20 (d, J=5.5 Hz, 1H), 7.97 (d, J=16.0 Hz, 1H), 7.88 (s, 1H), 6.81 (d, J=16.0 Hz, 1H), 5.92-5.83 (m, 1H), 4.37-4.20 (m, 2H), 3.84 (s, 3H), 3.78 (s, 3H), 3.01-2.93 (m, 2H), 2.68 (s, 3H), 1.36 (t, J=7.0 Hz, 3H)

Example 22

Preparation of (E)-Methyl 3-(1-ethoxy-5-bromo-3-(2-methoxy-2-oxoethyl)-1,3-dihydrobenzo[c][1,2]oxaphosphol-7-yl-1-oxide)acrylate

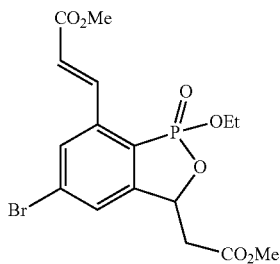 [SMILES: CCOP1(=O)OC(CC(=O)OC)c2cc(Br)cc(/C=C/C(=O)OC)c21]

A reaction was performed by the same method as in Example 1 except for using 4-bromophenyl phosphonic monoethyl ester (53.0 mg, 0.2 mmol) instead of 2-methylphenylphosphonic monoethyl ester of Example 1, thereby obtaining (E)-methyl 3-(1-ethoxy-5-bromo-3-(2-methoxy-2-oxoethyl)-1,3-dihydrobenzo[c][1,2]oxaphosphol-7-yl-1-oxide)acrylate (51.1 mg, 59%) corresponding to the target compound.

¹H NMR (400 MHz, CDCl₃) δ 7.85 (d, J=16.1 Hz, 1H), 7.82-7.80 (m, 1H), 7.50 (s, 1H), 6.71 (d, J=16.1 Hz, 1H), 5.84-5.75 (m, 1H), 4.36-4.16 (m, 2H), 3.82 (s, 3H), 3.78 (s, 3H), 2.96-2.94 (m, 2H), 1.35 (t, J=7.0 Hz, 3H)

Example 23

Preparation of Methyl 2-(1-ethoxy-2-phenyl-2,3-dihydro-1H-2,1-benzazaphosphol-3-yl-1-oxide)acetate

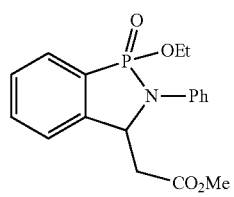 [SMILES: CCOP1(=O)c2ccccc2C(CC(=O)OC)N1c1ccccc1]

Ethyl N-phenyl P-phenylphosphonamidate (52.3 mg, 0.2 mmol) and methyl acrylate (36.0 μL, 0.4 mmol), which were starting materials, were put into a V-vial in the presence of [Rh(C₅Me₅)Cl₂]₂ (5.0 mg, 0.008 mmol), TEMPO (62.9 mg, 0.4 mmol), cesium pivalate (35.1 mg, 0.15 mmol), xylene (0.8 mL) was dropped therein as a solvent, and then, a reaction was performed at 110° C. for 20 hours. When the reaction was terminated, the solvent was removed, and then the resultant was separated using column chromatography, thereby obtaining methyl 2-(1-ethoxy-2-phenyl-2,3-dihydro-1H-2,1-benzazaphosphol-3-yl-1-oxide)acetate (94.9 mg, 92%) corresponding to the title compound.

¹H NMR (400 MHz, CDCl₃) δ 7.84-7.79 (m, 1H), 7.62-7.59 (m, 1H), 7.54-7.50 (m, 1H), 7.48 (d, J=8.1 Hz, 2H), 7.46-7.43 (m, 1H), 7.39 (t, J=7.9 Hz, 2H), 7.15-7.10 (m, 1H), 5.58-5.50 (m, 1H), 3.94-3.72 (m, 2H), 3.673 (s, 3H), 3.04 (dd, J=16.3, 3.4 Hz, 1H), 2.60 (dd, J=16.3, 8.6 Hz, 1H), 1.08 (t, J=7.0 Hz, 3H)

Example 24

Preparation of Methyl 2-(1-ethoxy-7-methyl-2-phenyl-2,3-dihydro-1H-2,1-benzazaphosphol-3-yl-1-oxide)acetate

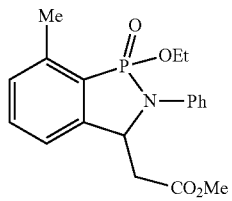 [SMILES: CCOP1(=O)c2c(C)cccc2C(CC(=O)OC)N1c1ccccc1]

A reaction was performed by the same method as in Example 23 except for using ethyl N-phenyl-P-(ortho-tolyl)phosphonamidate (55.1 mg, 0.2 mmol) instead of ethyl N-phenyl P-phenylphosphonamidate of Example 23, thereby obtaining methyl 2-(1-ethoxy-7-methyl-2-phenyl-2,3-dihydro-1H-2,1-benzazaphosphol-3-yl-1-oxide)acetate (62.5 mg, 87%) corresponding to the title compound.

¹H NMR (400 MHz, CDCl₃) δ 7.50-7.45 (m, 3H), 7.39 (t, J=7.9 Hz, 2H), 7.28-7.19 (m, 2H), 7.12 (t, J=7.3 Hz, 1H), 5.54-5.46 (m, 1H), 3.86-3.70 (m, 2H), 3.67 (s, 3H), 3.03 (dd, J=16.3, 3.3 Hz, 1H), 2.63 (s, 3H), 2.56 (dd, J=16.3, 8.6 Hz, 1H), 1.04 (t, J=7.1 Hz, 3H)

Example 25

Preparation of Methyl 2-(1-ethoxy-6-methyl-2-phenyl-2,3-dihydro-1H-2,1-benzazaphosphol-3-yl-1-oxide)acetate

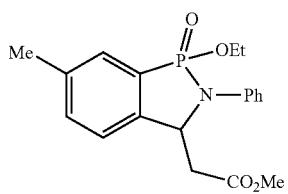 [SMILES: CCOP1(=O)c2cc(C)ccc2C(CC(=O)OC)N1c1ccccc1]

A reaction was performed by the same method as in Example 23 except for using ethyl N-phenyl-P-(metha-tolyl)phosphonamidate (55.1 mg, 0.2 mmol) instead of ethyl N-phenyl P-phenylphosphonamidate of Example 23, thereby obtaining methyl 2-(1-ethoxy-6-methyl-2-phenyl-2,3-dihydro-1H-2,1-benzazaphosphol-3-yl-1-oxide)acetate (68.3 mg, 95%) corresponding to the title compound.

¹H NMR (400 MHz, CDCl₃) δ 7.59 (d, J=11.2 Hz, 1H), 7.47 (d, J=8.6 Hz, 2H), 7.41-7.36 (m, 3H), 7.33-7.29 (m, 1H), 7.13-7.08 (m, 1H), 5.54-5.45 (m, 1H), 3.91-3.71 (m, 2H), 3.67 (s, 3H), 3.03 (dd, J=16.3, 3.3 Hz, 1H), 2.56 (dd, J=16.3, 8.7 Hz, 1H), 2.44 (s, 3H), 1.08 (t, J=7.1 Hz, 3H)

Example 26

Preparation of Methyl 2-(1-ethoxy-5-methoxy-2-phenyl-2,3-dihydro-1H-2,1-benzazaphosphol-3-yl-1-oxide)acetate

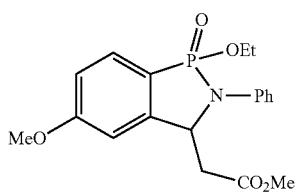

A reaction was performed by the same method as in Example 23 except for using ethyl N-phenyl-P-(para methoxyphenyl)phosphonamide (58.3 mg, 0.2 mmol) instead of ethyl N-phenyl P-phenylphosphonamidate of Example 23, thereby obtaining methyl 2-(1-ethoxy-5-methoxy-2-phenyl-2,3-dihydro-1H-2,1-benzazaphosphol-3-yl-1-oxide)acetate (37.5 mg, 50%) corresponding to the title compound.

$^1$H NMR (400 MHz, CDCl$_3$) δ 7.70 (dd, J=8.5, 10.2 Hz, 1H), 7.46 (dd, J=7.8, 0.8 Hz, 2H), 7.40-7.36 (m, 2H), 7.31-7.29 (m, 2H), 6.94 (t, J=2.5 Hz, 1H), 5.53-5.45 (m, 1H), 3.86 (s, 3H), 3.85-3.64 (m, 2H), 3.69 (s, 3H), 3.04 (dd, J=7.8, 3.3 Hz, 1H), 2.59 (dd, J=16.5, 8.8 Hz, 1H), 1.06 (t, J=7.1 Hz, 3H)

Example 27

Preparation of Methyl 2-(1-ethoxy-5-fluoro-2-phenyl-2,3-dihydro-1H-2,1-benzazaphosphol-3-yl-1-oxide)acetate

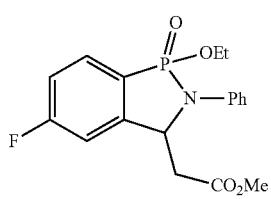 [SMILES: CCOP1(=O)c2ccc(F)cc2C(CC(=O)OC)N1c1ccccc1]

A reaction was performed by the same method as in Example 23 except for using ethyl N-phenyl-P-(para fluorophenyl)phosphonamide (55.9 mg, 0.2 mmol) instead of ethyl N-phenyl P-phenylphosphonamidate of Example 23, thereby obtaining methyl 2-(1-ethoxy-5-fluoro-2-phenyl-2,3-dihydro-1H-2,1-benzazaphosphol-3-yl-1-oxide)acetate (59.6 mg, 82%) corresponding to the title compound.

$^1$H NMR (400 MHz, CDCl$_3$) δ 7.82-7.76 (m, 1H), 7.46 (d, J=8.2 Hz, 2H), 7.39 (t, J=7.9 Hz, 2H), 7.25-7.11 (m, 3H), 5.55-5.46 (m, 1H), 3.94-3.73 (m, 2H), 3.70 (s, 3H), 3.05 (dd, J=16.7, 3.0 Hz, 1H), 2.60 (dd, J=16.7, 8.9 Hz, 1H), 1.08 (t, J=7.0 Hz, 3H)

Example 28

Preparation of Methyl 2-(5-chloro-1-ethoxy-2-phenyl-2,3-dihydro-1H-2,1-benzazaphosphol-3-yl-1-oxide)acetate

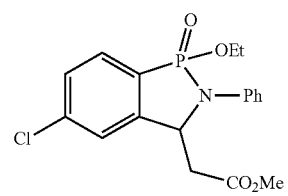 [SMILES: CCOP1(=O)c2ccc(Cl)cc2C(CC(=O)OC)N1c1ccccc1]

A reaction was performed by the same method as in Example 23 except for using ethyl N-phenyl-P-(para-chlorophenyl)phosphonamide (59.1 mg, 0.2 mmol) instead of ethyl N-phenyl P-phenylphosphonamidate of Example 23, thereby obtaining methyl 2-(5-chloro-1-ethoxy-2-phenyl-2,3-dihydro-1H-2,1-benzazaphosphol-3-yl-1-oxide)acetate (74.4 mg, 98%) corresponding to the title compound.

$^1$H NMR (400 MHz, CDCl$_3$) δ 7.71 (d, J=10.5 Hz, 1H), 7.52-7.37 (m, 6H), 7.16-7.12 (m, 1H), 5.53-5.44 (m, 1H), 3.95-3.74 (m, 2H), 3.689 (s, 3H), 3.03 (dd, J=16.7, 3.3 Hz, 1H), 2.60 (dd, J=16.6, 8.6 Hz, 1H), 1.08 (t, J=7.1 Hz, 3H); $^{31}$P NMR (161 MHz, CDCl$_3$) δ 26.2

Example 29

Preparation of Methyl 2-(1-ethoxy-6-trifluoromethyl-2-phenyl-2,3-dihydro-1H-2,1-benzazaphosphol-3-yl-1-oxide)acetate

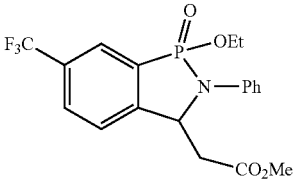 [SMILES: CCOP1(=O)c2cc(C(F)(F)F)ccc2C(CC(=O)OC)N1c1ccccc1]

A reaction was performed by the same method as in Example 23 except for using ethyl N-phenyl-P-(metha-trifluoromethylphenyl)phosphonamide (65.9 mg, 0.2 mmol) instead of ethyl N-phenyl P-phenylphosphonamidate of Example 23, thereby obtaining Methyl 2-(1-ethoxy-6-trifluoromethyl-2-phenyl-2,3-dihydro-1H-2,1-benzazaphosphol-3-yl-1-oxide)acetate (67.8 mg, 82%) corresponding to the title compound.

$^1$H NMR (400 MHz, CDCl$_3$) δ 8.06 (d, J=11.1 Hz, 1H), 7.84 (d, J=8.2 Hz, 1H), 7.63-7.61 (m, 1H), 7.47 (d, J=8.6 Hz, 2H), 7.41 (t, J=7.9 Hz, 2H), 7.19-7.14 (m, 1H), 5.60-5.50 (m,

1H), 4.04-3.85 (m, 2H), 3.68 (s, 3H), 3.05 (dd, J=16.6, 3.3 Hz, 1H), 2.62 (dd, J=16.6, 8.6 Hz, 1H), 1.11 (t, J=7.0 Hz, 3H)

Example 30

Preparation of Methyl 2-(1-ethoxy-5-nitro-2-phenyl-2,3-dihydro-1H-2,1-benzazaphosphol-3-yl-1-oxide)acetate

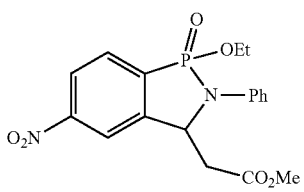 [SMILES: CCOP1(=O)c2ccc([N+](=O)[O-])cc2C(CC(=O)OC)N1c1ccccc1]

A reaction was performed by the same method as in Example 23 except for using ethyl N-phenyl-P-(para nitrophenyl)phosphonamidate (61.3 mg, 0.2 mmol) instead of ethyl N-phenyl P-phenylphosphonamidate of Example 23, thereby obtaining methyl 2-(1-ethoxy-5-nitro-2-phenyl-2,3-dihydro-1H-2,1-benzazaphosphol-3-yl-1-oxide)acetate (41.4 mg, 53%) corresponding to the title compound.

$^1$H NMR (400 MHz, CDCl$_3$) δ 8.39-8.34 (m, 2H), 7.98 (t, J=9.2 Hz, 1H), 7.48-7.40 (m, 4H), 7.20 (t, J=6.7 Hz, 1H), 5.63-5.52 (m, 1H), 4.08-3.85 (m, 2H), 3.69 (s, 3H), 3.11-3.04 (m, 1H), 2.69-2.58 (m, 1H), 1.12 (t, J=7.0 Hz, 3H)

Example 31

Preparation of Methyl 2-(5-acetyl-1-ethoxy-2-phenyl-2,3-dihydro-1H-2,1-benzazaphosphol-3-yl-1-oxide)acetate

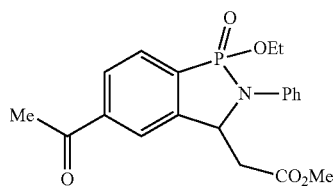 [SMILES: CCOP1(=O)c2ccc(C(C)=O)cc2C(CC(=O)OC)N1c1ccccc1]

A reaction was performed by the same method as in Example 23 except for using ethyl N-phenyl-P-(para acetylphenyl)phosphonamidate (60.7 mg, 0.2 mmol) instead of ethyl N-phenyl P-phenylphosphonamidate of Example 23, thereby obtaining methyl 2-(5-acetyl-1-ethoxy-2-phenyl-2,3-dihydro-1H-2,1-benzazaphosphol-3-yl-1-oxide)acetate (68.2 mg, 88%) corresponding to the title compound.

$^1$H NMR (400 MHz, CDCl$_3$) δ 8.09-8.06 (m, 1H), 8.04-8.02 (m, 1H), 7.91 (d, J=10.5 Hz, 1H), 7.48 (d, J=8.4 Hz, 2H), 7.41 (t, J=8.0 Hz, 2H), 7.18-7.14 (m, 1H), 5.61-5.51 (m, 1H), 4.00-3.78 (m, 2H), 3.68 (s, 3H), 3.09-3.03 (m, 1H), 2.66 (s, 3H), 2.67-2.55 (m, 1H), 1.09 (t, J=7.1 Hz, 3H)

Example 32

Preparation of Methyl 2-(1-ethoxy-6,7-dimethyl-2-phenyl-2,3-dihydro-1H-2,1-benzazaphosphol-3-yl-1-oxide)acetate

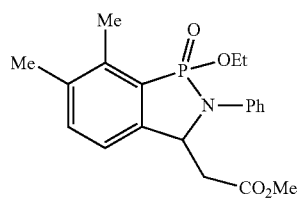 [SMILES: CCOP1(=O)c2c(ccc(C)c2C)C(CC(=O)OC)N1c1ccccc1]

A reaction was performed by the same method as in Example 23 except for using ethyl N-phenyl-P-(2,3-dimethylphenyl)phosphonamidate (57.9 mg, 0.2 mmol) instead of ethyl N-phenyl P-phenylphosphonamidate of Example 23, thereby obtaining methyl 2-(1-ethoxy-6,7-dimethyl-2-phenyl-2,3-dihydro-1H-2,1-benzazaphosphol-3-yl-1-oxide)acetate (73.2 mg, 98%) corresponding to the title compound.

$^1$H NMR (400 MHz, CDCl$_3$) δ 7.49 (d, J=8.4 Hz, 2H), 7.40-7.31 (m, 3H), 7.15-7.09 (m, 2H), 5.49-5.41 (m, 1H), 3.85-3.70 (m, 2H), 3.67 (s, 3H), 3.02 (dd, J=16.1, 3.4 Hz, 1H), 2.58-2.51 (m, 1H), 2.54 (s, 3H), 2.46 (s, 3H), 1.03 (t, J=7.0 Hz, 3H)

Example 33

Preparation of Methyl 2-(1-ethoxy-5,7-difluoro-2-phenyl-2,3-dihydro-1H-2,1-benzazaphosphol-3-yl-1-oxide)acetate

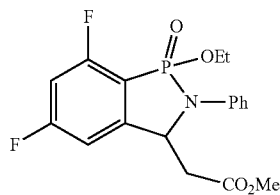 [SMILES: CCOP1(=O)c2c(F)cc(F)cc2C(CC(=O)OC)N1c1ccccc1]

A reaction was performed by the same method as in Example 23 except for using ethyl N-phenyl-P-(2,4-difluorophenyl)phosphonamidate (59.4 mg, 0.2 mmol) instead of ethyl N-phenyl P-phenylphosphonamidate of Example 23, thereby obtaining methyl 2-(1-ethoxy-5,7-difluoro-2-phenyl-2,3-dihydro-1H-2,1-benzazaphosphol-3-yl-1-oxide)acetate (41.9 mg, 55%) corresponding to the title compound.

$^1$H NMR (400 MHz, CDCl$_3$) δ 7.44-7.37 (m, 4H), 7.18-7.14 (m, 1H), 7.03-7.00 (m, 1H), 6.93-6.87 (m, 1H), 5.51-

5.41 (m, 1H), 4.18-4.00 (m, 2H), 3.69 (s, 3H), 3.02 (dd, J=16.7, 3.2 Hz, 1H), 2.62 (dd, J=16.7, 8.9 Hz, 1H), 1.16 (t, J=7.1 Hz, 3H)

Example 34

Preparation of Methyl 2-(1-ethoxy-2-phenyl-1,3-dihydronaphtho[2,3-c][1,2]azaphosphol-3-yl-1-oxide)acetate

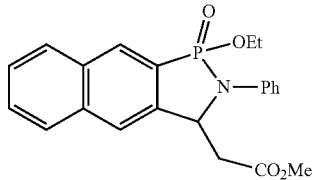 [SMILES: CCOP1(=O)c2cc3ccccc3cc2C(CC(=O)OC)N1c1ccccc1]

A reaction was performed by the same method as in Example 23 except for using ethyl N-phenyl β-naphthalene-2-yl-phosphonamidate (62.3 mg, 0.2 mmol) instead of ethyl N-phenyl P-phenylphosphonamidate of Example 23, thereby obtaining methyl 2-(1-ethoxy-2-phenyl-1,3-dihydronaphtho[2,3-c][1,2]azaphosphol-3-yl-1-oxide)acetate (57.7 mg, 73%) corresponding to the title compound.

$^1$H NMR (400 MHz, CDCl$_3$) δ 8.37 (d, J=8.4 Hz, 1H), 7.99 (d, J=7.9 Hz, 1H), 7.92-7.89 (m, 2H), 7.64-7.56 (m, 2H), 7.54 (d, J=8.5 Hz, 2H), 7.43-7.40 (m, 2H), 7.15 (t, J=7.3 Hz, 1H), 5.77-5.68 (m, 1H), 3.95-3.73 (m, 2H), 3.70 (s, 3H), 3.13 (dd, J=16.5, 3.3 Hz, 1H), 2.69 (dd, J=16.5, 8.7 Hz, 1H), 1.40 (t, J=7.1 Hz, 3H)

Example 35

Preparation of Ethyl 2-(1-ethoxy-2-phenyl-2,3-dihydro-1H-2,1-benzazaphosphol-3-yl-1-oxide)acetate

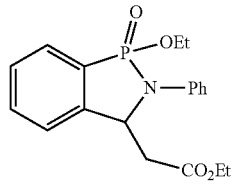 [SMILES: CCOC(=O)CC1c2ccccc2P(=O)(OCC)N1c1ccccc1]

A reaction was performed by the same method as in Example 23 except for using ethyl acrylate (43.6 μL, 0.4 mmol) instead of methyl acrylate of Example 23, thereby obtaining ethyl 2-(1-ethoxy-2-phenyl-2,3-dihydro-1H-2,1-benzazaphosphol-3-yl-1-oxide)acetate (59.7 mg, 83%) corresponding to the title compound.

$^1$H NMR (400 MHz, CDCl$_3$) δ 7.80 (dd, J=7.5, 10.8 Hz, 1H), 7.62-7.58 (m, 1H), 7.54-7.32 (m, 6H), 7.15-7.10 (m, 1H), 5.58-5.50 (m, 1H), 4.22-4.07 (m, 2H), 3.93-3.71 (m, 2H), 3.03 (dd, J=16.3, 3.4 Hz, 1H), 2.59 (dd, J=16.3, 8.5 Hz, 1H), 1.21 (t, J=7.5 Hz, 3H), 1.07 (t, J=7.0 Hz, 3H)

Example 36

Preparation of n-Butyl 2-(1-ethoxy-2-phenyl-2,3-dihydro-1H-2,1-benzazaphosphol-3-yl-1-oxide)acetate

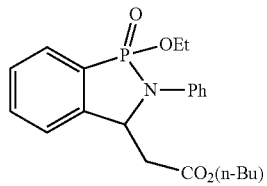

A reaction was performed by the same method as in Example 23 except for using n-butyl acrylate (57.1 μL, 0.4 mmol) instead of methyl acrylate of Example 23, thereby obtaining n-butyl 2-(1-ethoxy-2-phenyl-2,3-dihydro-1H-2,1-benzazaphosphol-3-yl-1-oxide)acetate (61.2 mg, 79%) corresponding to the target compound.

$^1$H NMR (400 MHz, CDCl$_3$) δ 7.83-7.78 (m, 1H), 7.62-7.58 (m, 1H), 7.54-7.37 (m, 4H), 7.41-7.37 (m, 2H), 7.14-7.10 (m, 1H), 5.59-5.51 (m, 1H), 4.14-4.02 (m, 2H), 3.91-3.71 (m, 2H), 3.04 (dd, J=16.3, 3.2 Hz, 1H), 2.59 (dd, J=16.3, 8.6 Hz, 1H), 1.60-1.53 (m, 2H), 1.39-1.28 (m, 2H), 1.08 (t, J=7.0 Hz, 3H), 0.91 (t, J=7.4 Hz, 3H)

Example 37

Preparation of 1-(1-Ethoxy-2-phenyl-2,3-dihydro-1H-2,1-benzazaphosphol-3-yl-1-oxide)propan-2-one

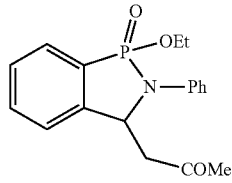

A reaction was performed by the same method as in Example 23 except for using methyl vinyl ketone (32.4 μL, 0.4 mmol) instead of methyl acrylate of Example 23, thereby obtaining 1-(1-ethoxy-2-phenyl-2,3-dihydro-1H-2,1-benzazaphosphol-3-yl-1-oxide)propan-2-one (57.3 mg, 87%) corresponding to the title compound.

$^1$H NMR (400 MHz, CDCl$_3$) δ 7.79 (dd, J=7.5, 10.7 Hz, 1H), 7.57 (tt, J=11.4, 1.3 Hz, 1H), 7.52-7.49 (m, 1H), 7.43-7.36 (m, 5H), 7.10 (tt, J=10.6, 1.3 Hz, 1H), 5.70-5.66 (m, 1H), 3.90-3.69 (m, 2H), 3.14 (dd, J=18.3, 2.5 Hz, 1H), 2.79 (dd, J=18.2, 8.8 Hz, 1H), 2.13 (s, 3H), 1.08 (t, J=7.1 Hz, 3H)

Example 38

Preparation of 2-(1-Ethoxy-2-phenyl-2,3-dihydro-1H-2,1-benzazaphosphol-3-yl-1-oxide)-N,N-dimethylacetamide

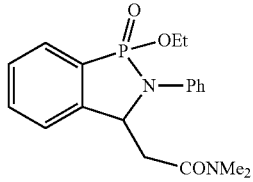

A reaction was performed by the same method as in Example 23 except for using N,N-dimethylacrylamide (41.2 µL, 0.4 mmol) instead of methyl acrylate of Example 23, thereby obtaining 2-(1-ethoxy-2-phenyl-2,3-dihydro-1H-2,1-benzazaphosphol-3-yl-1-oxide)-N,N-dimethylacetamide (51.6 mg, 72%) corresponding to the title compound.

$^1$H NMR (400 MHz, CDCl$_3$) δ 7.81-7.76 (m, 1H), 7.64-7.31 (m, 7H), 7.10-7.04 (m, 1H), 5.87-5.77 (m, 1H), 4.30-4.14 (m, 2H), 3.02-3.00 (m, 1H), 2.97 (s, 3H), 2.82 (s, 3H), 2.51 (dd, J=16.0, 9.0 Hz, 1H), 1.40 (t, J=7.1 Hz, 3H)

Example 39

Preparation of Methyl 2-(1,2-diphenyl-2,3-dihydro-1H-2,1-benzazaphosphol-3-yl-1-oxide)acetate

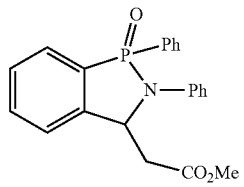 [SMILES: COC(=O)CC1c2ccccc2P(=O)(c2ccccc2)N1c1ccccc1]

A reaction was performed by the same method as in Example 23 except for using N,P,P-triphenylphosphonamide (52.3 mg, 0.2 mmol) instead of ethyl N-phenyl P-phenylphosphonamidate of Example 23, thereby obtaining methyl 2-(1,2-diphenyl-2,3-dihydro-1H-2,1-benzazaphosphol-3-yl-1-oxide)acetate (73.2 mg, 97%) corresponding to the title compound.

$^1$H NMR (400 MHz, CDCl$_3$) δ 7.85-7.79 (m, 1H), 7.67-7.22 (m, 13H), 5.81 (td, J=9.3, 3.1 Hz, 1H), 3.723 (s, 3H), 3.18 (dd, J=16.4, 3.2 Hz, 1H), 2.77 (dd, J=16.3, 9.0 Hz, 1H)

Example 40

Preparation of Methyl 2-(5-methoxy-1-p-methoxyphenyl-2-phenyl-2,3-dihydro-1H-2,1-benzazaphosphol-3-yl-1-oxide)acetate

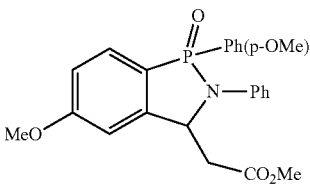

A reaction was performed by the same method as in Example 23 except for using P,P-bis(4-methoxyphenyl)-N-phenyl phosphinamide (70.7 mg, 0.2 mmol) instead of ethyl N-phenyl phenylphosphonamidate of Example 23, thereby obtaining methyl 2-(5-methoxy-1-p-methoxyphenyl-2-phenyl-2,3-dihydro-1H-2,1-benzazaphosphol-3-yl-1-oxide)acetate (59.5 mg, 90%) corresponding to the title compound.

$^1$H NMR (400 MHz, CDCl$_3$) δ 7.56-7.48 (m, 2H), 7.36 (d, J=8.5 Hz, 2H), 7.24-7.20 (m, 3H), 7.00-6.93 (m, 3H), 6.82-6.78 (m, 2H), 5.74-5.69 (m, 1H), 3.86 (s, 3H), 3.75 (s, 3H), 3.72 (s, 3H), 3.17 (dd, J=16.4, 3.1 Hz, 1H), 2.75 (dd, J=16.4, 9.0 Hz, 1H)

Example 41

Preparation of Methyl 2-(5-fluoro-1-p-fluorophenyl-2-phenyl-2,3-dihydro-1H-2,1-benzazaphosphol-3-yl-1-oxide)acetate

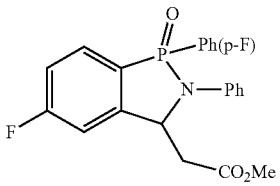

A reaction was performed by the same method as in Example 23 except for using P,P-bis(4-fluorophenyl)-N-phenyl phosphinamide (65.9 mg, 0.2 mmol) instead of ethyl N-phenyl phenylphosphonamidate of Example 23, thereby obtaining a mixture (59.8 mg, 94%) of methyl 2-(5-fluoro-1-p-fluorophenyl-2-phenyl-2,3-dihydro-1H-2,1-benzazaphosphol-3-yl-1-oxide)acetate corresponding to the title compound.

$^1$H NMR (400 MHz, CDCl$_3$) δ 7.65-7.56 (m, 3H), 7.35 (d, J=8.2 Hz, 2H), 7.27-7.23 (m, 4H), 7.21-7.15 (m, 1H), 7.01 (t,

J=8.7 Hz, 2H), 5.74 (td, J=14.4, 3.1 Hz, 1H), 3.73 (s, 3H), 3.16 (dd, J=16.6, 3.1 Hz, 1H), 2.76 (dd, J=16.7, 9.1 Hz, 1H)

Example 42

Preparation of n-Butyl 2-(1,2-diphenyl-2,3-dihydro-1H-2,1-benzazaphosphol-3-yl-1-oxide)acetate

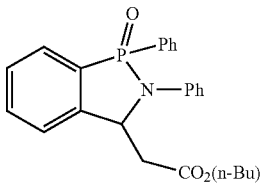

A reaction was performed by the same method as in Example 23 except for using N,P,P-triphenylphosphinamide (52.3 mg, 0.2 mmol) instead of ethyl N-phenyl phenylphosphonamidate of Example 23 and using n-butyl acrylate (57.1 μL, 0.4 mmol) instead of methyl acrylate of Example 23, thereby obtaining n-butyl 2-(1,2-diphenyl-2,3-dihydro-1H-2,1-benzazaphosphol-3-yl-1-oxide)acetate (73.0 mg, 87%) corresponding to the title compound.

$^1$H NMR (400 MHz, CDCl$_3$) δ 7.66-7.57 (m, 4H), 7.52 (dd, J=1.9, 7.8 Hz, 1H), 7.44 (td, J=11.0, 4.1 Hz, 1H), 7.41-7.37 (m, 3H), 7.31 (td, J=7.5, 3.4 Hz, 2H), 7.23 (t, J=7.7 Hz, 2H), 6.97 (t, J=7.4 Hz, 1H), 5.79 (td, J=14.1, 3.1 Hz, 1H), 4.19-4.07 (m, 2H), 3.18 (dd, J=16.3, 3.2 Hz, 1H), 2.75 (dd, J=16.3, 3.2 Hz, 1H), 1.60 (q, J=6.8 Hz, 2H), 1.39-1.29 (m, 2H), 0.92 (t, J=7.4 Hz, 3H)

Example 43

Preparation of 1-(1,2-Diphenyl-2,3-dihydro-1H-2,1-benzazaphosphol-3-yl-1-oxide)propan-2-one

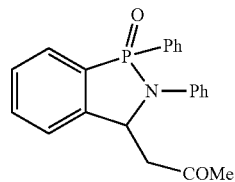

A reaction was performed by the same method as in Example 23 except for using N,P,P-triphenylphosphinamide (52.3 mg, 0.2 mmol) instead of ethyl N-phenyl phenylphosphonamidate of Example 23 and using methyl vinyl ketone (32.4 μL, 0.4 mmol) instead of methyl acrylate of Example 23, thereby obtaining 1-(1,2-diphenyl-2,3-dihydro-1H-2,1-benzazaphosphol-3-yl-1-oxide)propan-2-one (73.0 mg, 87%) corresponding to the title compound.

$^1$H NMR (400 MHz, CDCl$_3$) δ 7.86-7.80 (m, 2H), 7.63 (dd, J=7.4, 9.6 Hz, 3H), 7.59-7.46 (m, 5H), 7.24 (dd, J=7.2, 8.3 Hz, 3H), 7.04-7.01 (m, 3H), 5.96 (d, J=8.8 Hz, 1H), 3.31 (dd, J=18.0, 2.1 Hz, 1H), 2.85 (dd, J=18.0, 8.9 Hz, 1H), 2.22 (s, 3H)

Example 44

Preparation of 2-(1,2-Diphenyl-2,3-dihydro-1H-2,1-benzazaphosphol-3-yl-1-oxide)-N,N-dimethylacetamide

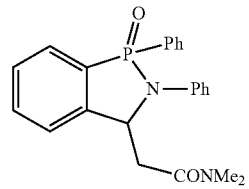

A reaction was performed by the same method as in Example 23 except for using N,P,P-triphenylphosphinamide (52.3 mg, 0.2 mmol) instead of ethyl N-phenyl phenylphosphonamidate of Example 23 and using N,N-dimethylacrylamide (41.2 μL, 0.4 mmol) instead of methyl acrylate of Example 23, thereby obtaining 2-(1,2-diphenyl-2,3-dihydro-1H-2,1-benzazaphosphol-3-yl-1-oxide)-N,N-dimethylacetamide (66.4 mg, 85%) corresponding to the title compound.

$^1$H NMR (400 MHz, CDCl$_3$) δ 7.88-7.82 (m, 2H), 7.67-7.11 (m, 11H), 6.98 (t, J=7.3 Hz, 1H), 6.11 (t, J=8.9 Hz, 1H), 3.14 (dd, J=16.1, 2.3 Hz, 1H), 3.02 (s, 3H), 2.86 (s, 3H), 2.66 (dd, J=16.1, 9.0 Hz, 1H)

Example 45

Preparation of 2-(1,2-Diphenyl-2,3-dihydro-1H-2,1-benzazaphosphol-3-yl-1-oxide)acetonitrile

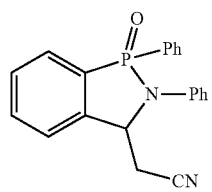 [SMILES: N#CCC1c2ccccc2P(=O)(c2ccccc2)N1c1ccccc1]

A reaction was performed by the same method as in Example 23 except for using N,P,P-triphenylphosphinamide (52.3 mg, 0.2 mmol) instead of ethyl N-phenyl phenylphosphonamidate of Example 23 and using acrylonitrile (26.3 μL, 0.4 mmol) instead of methyl acrylate of Example 23, thereby obtaining 2-(1,2-diphenyl-2,3-dihydro-1H-2,1-benzazaphosphol-3-yl-1-oxide)acetonitrile (63.4 mg, 92%) corresponding to the title compound.

$^1$H NMR (400 MHz, CDCl$_3$) δ 7.92-7.89 (m, 1H), 7.72-7.68 (m, 2H), 7.61-7.54 (m, 3H), 7.42-7.26 (m, 7H), 7.05 (t,

J=7.3 Hz, 1H), 5.51 (td, J=14.3, 2.9 Hz, 1H), 3.19 (dd, J=16.8, 3.2 Hz, 1H), 2.73 (dd, J=16.8, 9.3 Hz, 1H)

Example 46

Preparation of 1,2-Diphenyl-3-(phenylsulfonylmethyl)-2,3-dihydro-1H-2,1-benzazaphosphol-1-oxide

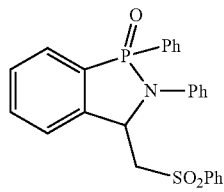

A reaction was performed by the same method as in Example 23 except for using N,P,P-triphenylphosphinamide (52.3 mg, 0.2 mmol) instead of ethyl N-phenyl phenylphosphonamidate of Example 23 and using phenyl vinyl sulfone (67.3 mg, 0.4 mmol) instead of methyl acrylate of Example 23, thereby obtaining 1,2-diphenyl-3-(phenylsulfonylmethyl)-2,3-dihydro-1H-2,1-benzazaphosphol-1-oxide (81.8 mg, 89%) corresponding to the title compound.

$^1$H NMR (400 MHz, CDCl$_3$) δ 8.30 (ddd, J=7.9, 2.9, 0.6 Hz, 1H), 7.89-7.86 (m, 2H), 7.73-7.29 (m, 13H), 7.19 (t, J=8.0 Hz, 2H), 6.97 (t, J=7.4 Hz, 1H), 5.96 (t, 8.9 Hz, 1H), 3.76 (dd, J=14.5, 1.1 Hz, 1H), 3.57 (dd, J=14.5, 8.6 Hz, 1H)

Example 47

Preparation of methyl 2-(1-Ethoxy-2,5-diphenyl-2,3-dihydro-1H-2,1-azaphosphol-3-yl-1-oxide)acetate

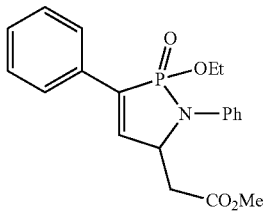 [SMILES: CCOP1(=O)C(c2ccccc2)=CC(CC(=O)OC)N1c1ccccc1]

Ethyl N-phenyl-P-(1-(phenyl)vinyl)phosphonamidate (57.5 mg, 0.2 mmol), which was a starting material, was put into a V-vial in the presence of [Rh(C$_5$Me$_5$)Cl$_2$]$_2$ (5.0 mg, 0.008 mmol), Cu(OAc)$_2$ (36.4 mg, 0.2 mmol), and cesium acetate (130.3 mg, 0.4 mmol), dichloroethane (0.8 mL) was dropped therein as a solvent, and then a reaction was performed at 80° C. for 30 hour. When the reaction was terminated, the solvent was removed, and then the resultant was separated using column chromatography, thereby obtaining methyl 2-(1-ethoxy-2,5-diphenyl-2,3-dihydro-1H-2,1-azaphosphol-3-yl-1-oxide)acetate (40.1 mg, 54%) corresponding to the title compound.

$^1$H NMR (400 MHz, CDCl$_3$) δ 7.75-7.72 (m, 2H), 7.44-7.36 (m, 6H), 7.31 (dd, J=9.3, 2.5 Hz, 1H), 7.26-7.19 (m, 1H), 7.13-7.09 (m, 1H), 5.01-4.96 (m, 1H), 3.88-3.79 (m, 2H), 3.71 (s, 3H), 3.07 (dd, J=16.5, 3.7 Hz, 1H), 2.43 (dd, J=16.5, 10.4 Hz, 1H), 1.00 (t, J=7.1 Hz, 3H)

Example 48

Preparation of Methyl 2-(1-ethoxy-5-p-methylphenyl-2-phenyl-2,3-dihydro-1H-2,1-azaphosphol-3-yl-1-oxide)acetate

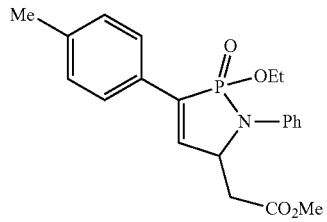 [SMILES: CCOP1(=O)C(c2ccc(C)cc2)=CC(CC(=O)OC)N1c1ccccc1]

A reaction was performed by the same method as in Example 47 except for using ethyl N-phenyl-P-(1-(paratolyl)vinyl)phosphonamidate (60.3 mg, 0.2 mmol) instead of ethyl N-phenyl-P-(1-phenylvinyl)phosphonamidate of Example 47, thereby obtaining methyl 2-(1-ethoxy-5-p-methylphenyl-2-phenyl-2,3-dihydro-1H-2,1-azaphosphol-3-yl-1-oxide)acetate (54.7 mg, 71%) corresponding to the title compound.

$^1$H NMR (400 MHz, CDCl$_3$) δ 7.64-7.62 (m, 2H), 7.40-7.35 (m, 1H), 7.28-7.27 (m, 1H), 7.25-7.21 (m, 3H), 7.16 (dd, J=9.6, 2.5 Hz, 1H), 7.12-7.08 (m, 1H), 5.02-4.95 (m, 1H), 3.86-3.76 (m, 2H), 3.70 (s, 3H), 3.06 (dd, J=11.5, 3.8 Hz, 1H), 2.42 (dd, J=10.6, 16.7 Hz, 1H), 2.37 (s, 3H), 0.99 (t, J=7.1 Hz, 3H)

Example 49

Preparation of Methyl 2-(1-ethoxy-5-p-chlorophenyl-2-phenyl-2,3-dihydro-1H-2,1-azaphosphol-3-yl-1-oxide)acetate

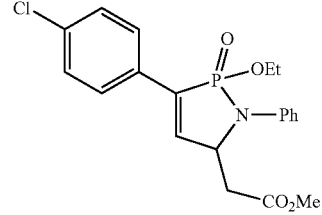 [SMILES: CCOP1(=O)C(c2ccc(Cl)cc2)=CC(CC(=O)OC)N1c1ccccc1]

A reaction was performed by the same method as in Example 47 except for using ethyl N-phenyl-P-(1-(para-chlorophenyl)vinyl)phosphonamidate (64.3 mg, 0.2 mmol) instead of ethyl N-phenyl-P-(1-phenylvinyl)phosphonamidate of Example 47, thereby obtaining methyl 2-(1-ethoxy-5-p-chlorophenyl-2-phenyl-2,3-dihydro-1H-2,1-azaphosphol-3-yl-1-oxide)acetate (43.0 mg, 53%) corresponding to the title compound.

$^1$H NMR (400 MHz, CDCl$_3$) δ 7.69-7.66 (m, 2H), 7.40-7.38 (m, 4H), 7.32 (d, J=2.6 Hz, 1H), 7.22 (d, J=2.5 Hz, 1H), 7.15-7.10 (m, 1H), 5.00-4.95 (m, 1H), 3.87-3.79 (m, 2H), 3.71 (s, 3H), 3.06 (dd, J=16.6, 3.7 Hz, 1H), 2.42 (dd, J=16.6, 10.5 Hz, 1H), 0.99 (t, J=7.1 Hz, 3H)

The dihydro-1H-phosphole 1-oxide derivatives according to the present invention have pharmacological and physiological activities, such that the dihydro-1H-phosphole 1-oxide derivatives may be used as important intermediates at the time of synthesizing various medicines as well as a crop protecting agent.

Further, in the preparation method of a dihydro-1H-phosphole 1-oxide derivative according to the present invention, various dihydro-1H-phosphole 1-oxide derivatives may be prepared with high yield by the simple synthesis process by reacting the phosphinic derivative and the vinyl derivative with each other in the presence of the rhodium (Rh) catalyst, the oxidant, and the base.

What is claimed is:

1. A dihydro-1H-phosphole 1-oxide derivative represented by the following Chemical Formula 1:

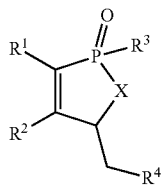

[Chemical Formula 1]

in Chemical Formula 1,

X is NR' or O;

R' is (C1-C20)alkyl or (C6-C20)aryl;

$R^1$ and $R^2$ are each independently hydrogen, (C1-C20)alkyl or (C6-C20)aryl, or are linked to each other by —$CR^{11}$=$CR^{12}$—$CR^{13}$=$CR^{14}$— to form a fused ring;

$R^{11}$ to $R^{14}$ are each independently hydrogen, (C1-C20)alkyl, halo(C1-C20)alkyl, (C1-C20)alkoxy, (C6-C20)aryl, halogen, (C1-C20)alkylcarbonyl, nitro, or (C1-C20)alkoxycarbonylethenyl, or are linked to a substituent adjacent thereto by (C1-C7)alkylene, (C2-C7)alkenylene, or (C4-C7)alkanedienylene to form a fused ring;

$R^3$ is (C1-C20)alkoxy or (C6-C20)aryl;

$R^4$ is (C1-C20)alkoxycarbonyl, (C6-C20)arylcarbonyl, (C1-C20)alkylcarbonyl, cyano, di(C1-C20)alkylcarbamoyl, di(C6-C20)arylcarbamoyl, (C6-C20)arylsulfonyl, (C1-C20)alkylsulfonyl, di(C1-C20)alkylphosphoryl, or di(C6-C20)arylphosphoryl; and alkyl and aryl of $R^1$ to $R^3$ are further substituted with one or more substituents selected from the group consisting of halogen, (C1-C20)alkyl, (C1-C20)alkoxy, and halo(C1-C20)alkyl, respectively.

2. The dihydro-1H-phosphole 1-oxide derivative of claim 1, wherein it is represented by Chemical Formula 2 or 3:

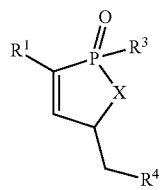

[Chemical Formula 2]

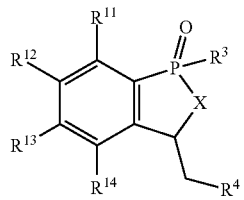

[Chemical Formula 3]

in Chemical Formulas 2 and 3, X, $R^3$, and $R^4$ have the same definitions as defined in claim 1;

$R^1$ is (C1-C20)alkyl or (C6-C20)aryl, alkyl or aryl of $R^1$ being further substituted with one or more substituents selected from the group consisting of halogen and (C1-C20)alkyl; and $R^{11}$ to $R^{14}$ are each independently hydrogen, (C1-C20)alkyl, halo(C1-C20)alkyl, (C1-C20)alkoxy, (C6-C20)aryl, halogen, (C1-C20)alkylcarbonyl, nitro, or (C1C20)alkoxycarbonylethenyl, or are linked to a substituent adjacent thereto by

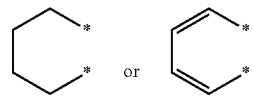

to form a fused ring.

3. The dihydro-1H-phosphole 1-oxide derivative of claim 2, wherein X is NR' or O; R' is methyl, ethyl, propyl, butyl, pentyl, hexyl, phenyl, or naphthyl;

$R^1$ is methyl, ethyl, propyl, butyl, pentyl, hexyl, heptyl, octyl, phenyl, naphthyl, or fluorenyl, phenyl, naphthyl, or fluorenyl of $R^1$ being further substituted with one or more substituents selected from the group consisting of methyl, ethyl, propyl, butyl, pentyl, hexyl, trifluoromethyl, methoxy, ethoxy, propoxy, butoxy, pentyloxy, hexyloxy, chloro, bromo, fluoro, or iodo;

$R^{11}$ to $R^{14}$ are each independently hydrogen, methyl, ethyl, propyl, butyl, pentyl, hexyl, trifluoromethyl, methoxy, ethoxy, propoxy, butoxy, pentyloxy, hexyloxy, phenyl, naphthyl, fluoro, chloro, iodo, bromo, acetyl, nitro, or ethoxycarbonylethenyl, or are linked to a substituent adjacent thereto by

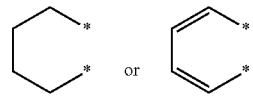 [SMILES: *CCCC* ; "or" ; */C=C\C=C/*]

to form a fused ring;

$R^3$ is methoxy, ethoxy, propoxy, butoxy, pentyloxy, hexyloxy, phenyl, or naphthyl, phenyl or naphthyl of $R^3$ being further substituted with one or more substituents selected from the group consisting of methyl, ethyl, propyl, butyl, pentyl, hexyl, trifluoromethyl, methoxy, ethoxy, propoxy, butoxy, pentyloxy, hexyloxy, chloro, bromo, fluoro, or iodo; and $R^4$ is methoxycarbonyl, ethoxycarbonyl, propoxycarbonyl, butoxycarbonyl, pentyloxycarbonyl, hexyloxycarbonyl, methylcarbonyl, ethylcarbonyl, propylcarbonyl, butylcarbonyl, pentylcarbonyl, hexylcarbonyl, cyano, dimethylcarbamoyl, diethylcarbamoyl, dipropylcarbamoyl, dibutylcarbamoyl, dipentylcarbamoyl, dihexylcarbamoyl, methylethylcarbamoyl, phenylsulfonyl, naphthylsulfonyl, dimethylphosphoryl, diethylphosphoryl, dipropylphosphoryl, dibutylphosphoryl, dipentylphosphoryl, dihexylphosphoryl, or methylethylphosphoryl.
4. The dihydro-1H-phosphole 1-oxide derivative of claim 3, wherein it is selected from the following compounds;
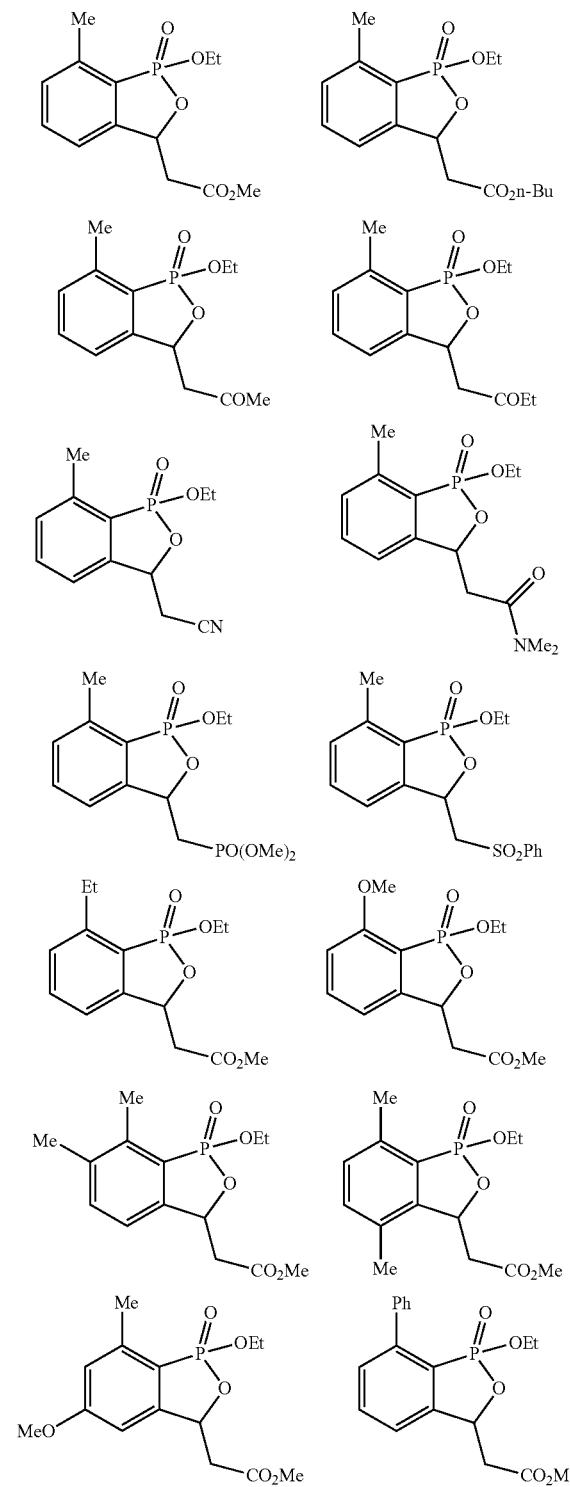
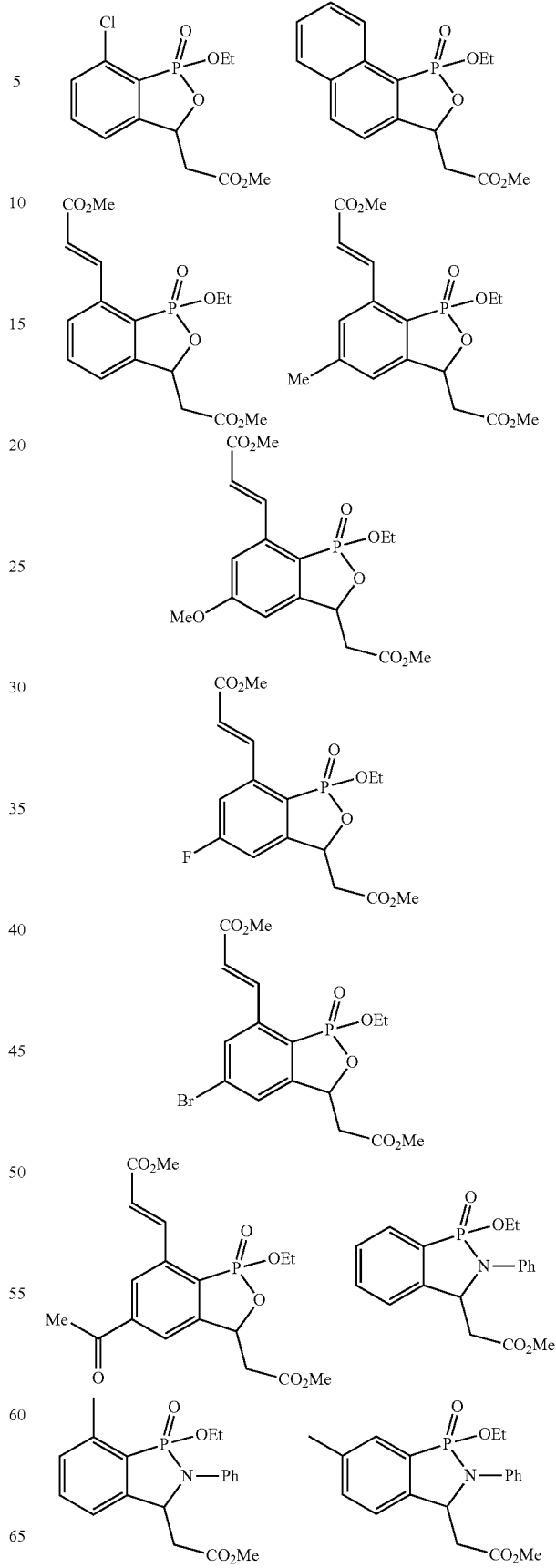

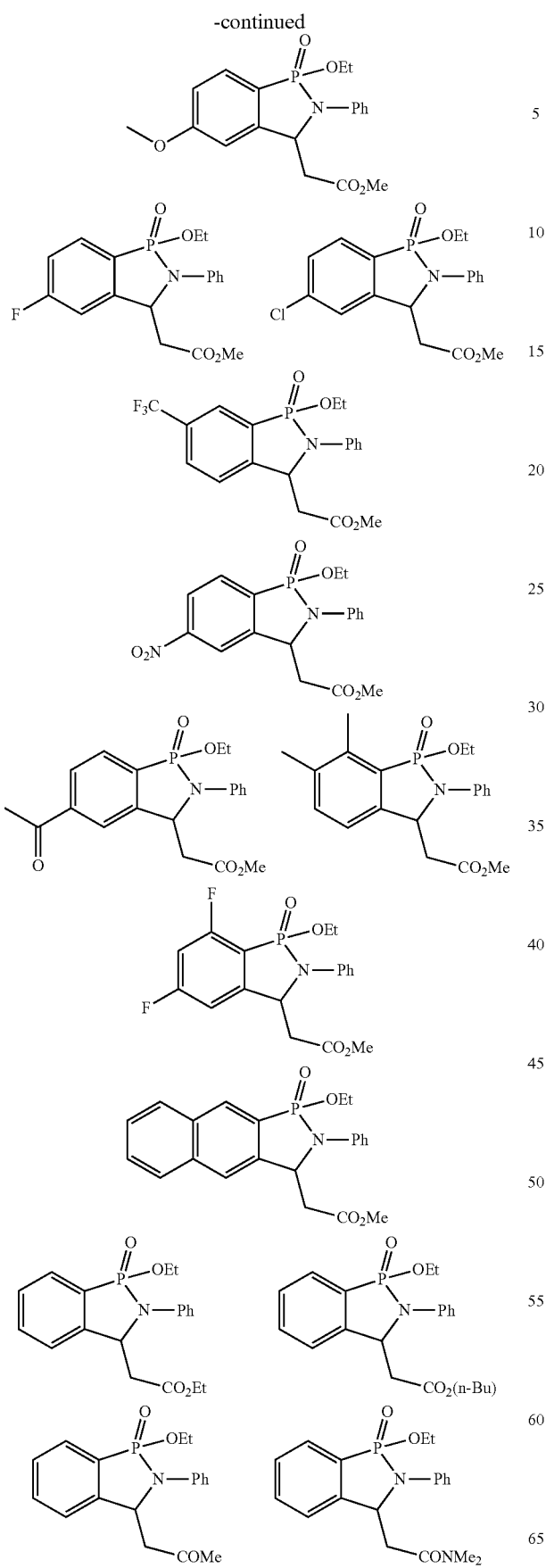
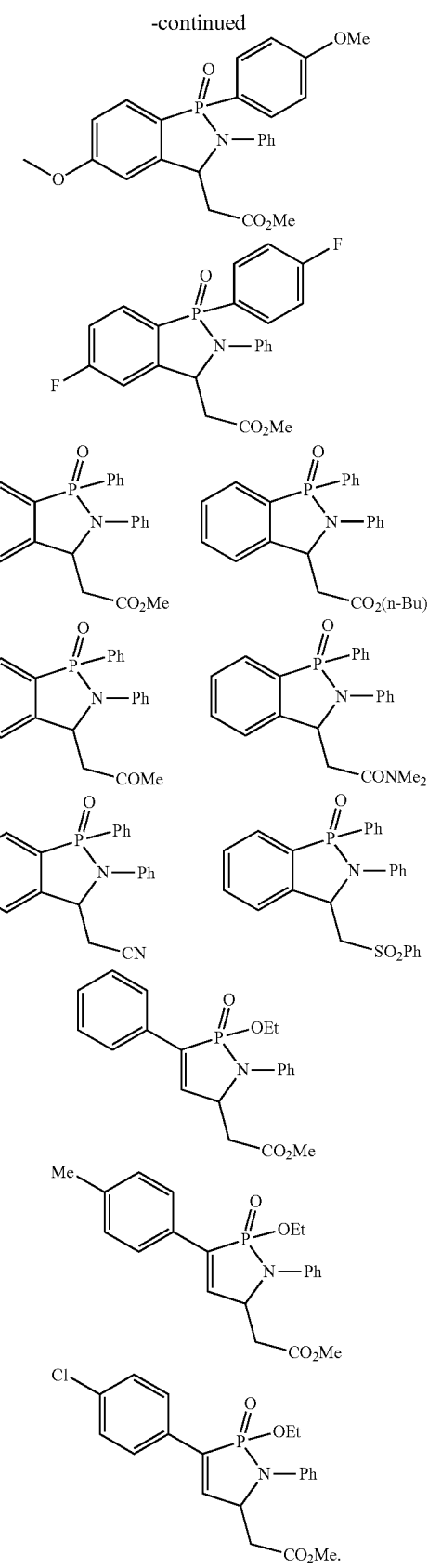
5. A preparation method of a dihydro-1H-phosphole 1-oxide derivative, the preparation method characterized by reacting a phosphinic derivative represented by the following Chemical Formula 4 and a vinyl derivative represented by the following Chemical Formula 5 with each other in the presence of a rhodium (Rh) catalyst, an oxidant, and a base to prepare a dihydro-1H-phosphole 1-oxide derivative represented by the following Chemical Formula 1:

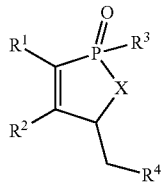

[Chemical Formula 1]

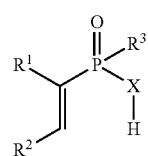

[Chemical Formula 4]

[Chemical Formula 5]

in Chemical Formulas 1, 4, and 5,

X is NR' or O;

R' is (C1-C20)alkyl or (C6-C20)aryl;

$R_1$ and $R^2$ are each independently hydrogen, (C1-C20)alkyl or (C6-C20)aryl, or are linked to each other by —$CR^{11}$=$CR^{12}$—$CR^{13}$=$CR^{14}$— to form a fused ring;

$R^{11}$ to $R^{14}$ are each independently hydrogen, (C1-C20)alkyl, halo(C1-C20)alkyl, (C1-C20)alkoxy, (C6-C20)aryl, halogen, (C1-C20)alkylcarbonyl, nitro, or (C1-C20)alkoxycarbonylethenyl, or are linked to a substituent adjacent thereto by (C1-C7)alkylene, (C2-C7)alkenylene, or (C4-C7)alkanedienylene to form a fused ring;

$R^3$ is (C1-C20)alkoxy or (C6-C20)aryl;

$R^4$ is (C1-C20)alkoxycarbonyl, (C6-C20)arylcarbonyl, (C1-C20)alkylcarbonyl, cyano, di(C1-C20)alkylcarbamoyl, di(C6-C20)arylcarbamoyl, (C6-C20)arylsulfonyl, (C1-C20)alkylsulfonyl, di(C1-C20)alkylphosphoryl, or di(C6-C20)arylphosphoryl; and alkyl and aryl of $R^1$ to $R^3$ are further substituted with one or more substituents selected from the group consisting of halogen, (C1-C20)alkyl, (C1-C20)alkoxy, and halo(C1-C20)alkyl, respectively.

6. The preparation method of claim 5, wherein the rhodium (Rh) catalyst is one or two or more selected from the group consisting of [RhCl(cod)]$_2$ (cod=1,5-cyclooctadiene), [RhCl(C$_2$H$_4$)$_2$]$_2$, Rh(aCaC)$_3$, RhCl$_3$, RhCl$_3$.xH$_2$O, RhBr$_3$.xH$_2$O, Rh$_2$O$_3$, Rh$_2$O$_3$.xH$_2$O, [(C$_5$Me$_5$)Rh(MeCN)$_3$][SbF$_6$]$_2$, [Rh(C$_5$Me$_5$)Cl$_2$]$_2$, (H$_2$NCH$_2$CH$_2$NH$_2$)$_3$RhCl$_3$.3H$_2$O, chlorobis(2-phenylpyridine)rhodium(III) dimer, dichloro(dimethylglyoximato)(dimethylglyoxime)rhodium(III), trichloro-[1,1,1-tri(diphenylphosphinomethyl)ethane]rhodium(III), RhI$_3$, rhodium(III) 2,4-pentenedionate, and Rh$_2$(SO$_4$)$_3$.4H$_2$O.

7. The preparation method of claim 5, wherein a use amount of the rhodium (Rh) catalyst is 0.01 to 0.2 equivalents with respect to the phosphinic derivative represented by Chemical Formula 4.

8. The preparation method of claim 5, wherein the oxidant is one or two or more selected from the group consisting of AgO, Ag$_2$O, AgOAc, Ag$_2$CO$_3$, AgSbF$_6$, AgOTf, Cu(OAc)$_2$.H$_2$O, CuCl, CuO, Cu$_2$O, CuOAc, Cu(OAc)$_2$, Cu(OTf)$_2$, Na$_2$S$_2$O$_8$, K$_2$S$_2$O$_8$, (NH$_4$)$_2$ S$_2$O$_8$, oxygen, 2,2,6,6-tetramethyl-1-piperidinyloxy(free radical) (TEMPO), NaOAc, p-benzoquinone, N-iodosuccinimide (NIS), N-chlorosuccinimide (NCS), N-bromosuccinimide (NBS), FeCl$_3$, Mn(OAc)$_3$.2H$_2$O, V$_2$O$_5$, PhI(OAc)$_2$, PhI(TFA)$_2$, IOAc, and ozone.

9. The preparation method of claim 5, wherein a use amount of the oxidant is 0.5 to 3.0 equivalents with respect to the phosphinic derivative represented by Chemical Formula 4.

10. The preparation method of claim 5, wherein the base is one or two or more selected from the group consisting of cesium fluoride [CsF], cesium pivalate [(CH$_3$)$_3$CCOOCs], cesium acetate [CH$_3$COOCs], lithium acetate [LiOAc], potassium acetate [CH$_3$COOK], sodium acetate [NaOAc], cesium carbonate [Cs$_2$CO$_3$], lithium carbonate [Li$_2$CO$_3$], sodium carbonate [Na$_2$CO$_3$], potassium carbonate [K$_2$CO$_3$], potassium phosphate monobasic [KH$_2$PO$_4$], potassium phosphate dibasic [K$_2$HPO$_4$], potassium phosphate tribasic [K$_3$PO$_4$], sodium phosphate dibasic dihydrate [Na$_2$HPO$_4$.2H$_2$O], sodium phosphate dibasic [Na$_2$HPO$_4$], and sodium phosphate monobasic [NaH$_2$PO$_4$].

11. The preparation method of claim 5, wherein a use amount of the base is 0.5 to 3.0 equivalents with respect to the phosphinic derivative represented by Chemical Formula 4.

12. The preparation method of claim 5, wherein a use amount of the vinyl derivative represented by Chemical Formula 5 is 1.0 to 3.0 equivalents with respect to the phosphinic derivative represented by Chemical Formula 4.

* * * * *